(12) United States Patent
Atalar et al.

(10) Patent No.: US 6,549,800 B1
(45) Date of Patent: Apr. 15, 2003

(54) METHODS FOR IN VIVO MAGNETIC RESONANCE IMAGING

(75) Inventors: Ergin Atalar, Columbia, MD (US); Paul A. Bottomley, Columbia, MD (US); Elias Zerhouin, Pasadena, MD (US); Henry Halperin, Baltimore, MD (US); Elliot McVeigh, Potomac, MD (US); Albert C. Lardo, Lutherville, MD (US)

(73) Assignee: Johns Hopkins Unversity School of Medicine, Baltimore, MD (US)

( * ) Notice: Subject to any disclaimer, the term of this patent is extended or adjusted under 35 U.S.C. 154(b) by 0 days.

(21) Appl. No.: 09/549,921

(22) Filed: Apr. 14, 2000

Related U.S. Application Data

(63) Continuation-in-part of application No. 09/536,090, filed on Mar. 24, 2000, and a continuation-in-part of application No. 09/360,144, filed on Jul. 26, 1999, which is a continuation-in-part of application No. 08/638,934, filed on Apr. 25, 1996, now Pat. No. 5,928,145.
(60) Provisional application No. 60/129,368, filed on Apr. 15, 1999, provisional application No. 60/129,364, filed on Apr. 15, 1999, and provisional application No. 60/192,133, filed on Mar. 24, 2000.

(51) Int. Cl.[7] .............................................. A61B 5/05
(52) U.S. Cl. ...................... 600/423; 600/407; 600/410; 600/415; 600/417; 600/424; 606/130; 324/301; 324/244; 324/256; 324/257; 324/260
(58) Field of Search ............................... 600/423, 407, 600/409, 410, 415, 417, 424; 324/300, 301, 302, 244, 256, 257, 260, 200; 606/130

(56) References Cited

U.S. PATENT DOCUMENTS

| | | | |
|---|---|---|---|
| 3,342,175 A | 9/1967 | Bulloch | 128/2 |
| 4,431,005 A | 2/1984 | McCormick | 128/656 |
| 4,445,501 A | 5/1984 | Bresler | 128/1.5 |
| 4,572,198 A | 2/1986 | Codrinton | 128/653 |
| 4,643,186 A | 2/1987 | Rosen et al. | 128/303.1 |
| 4,672,972 A | 6/1987 | Berke | 128/653 |
| 4,766,381 A | 8/1988 | Conturo et al. | 324/309 |
| 4,776,341 A | 10/1988 | Bachus et al. | 128/653 |
| 4,791,372 A | 12/1988 | Kirk et al. | 324/318 |
| 4,793,356 A | 12/1988 | Misic et al. | 128/653 |
| 4,813,429 A | 3/1989 | Eshel et al. | 128/736 |
| 4,823,812 A | 4/1989 | Eshel et al. | 128/804 |
| 4,858,613 A | 8/1989 | Fry et al. | 128/660.03 |

(List continued on next page.)

FOREIGN PATENT DOCUMENTS

| | | |
|---|---|---|
| EP | 0 659 385 A1 | 6/1995 |
| EP | 0 673 621 A1 | 9/1995 |
| EP | 0 768 539 A2 | 4/1997 |

(List continued on next page.)

OTHER PUBLICATIONS

Edelman et al., "Magnetic Resonance Imaging" NEJM. 328: 708–716 (1993).

(List continued on next page.)

Primary Examiner—Marvin M. Lateef
Assistant Examiner—Jeoyuh Lin
(74) Attorney, Agent, or Firm—Foley Hoag LLP

(57) ABSTRACT

The systems and methods of the present invention provide for MRI probes adapted for insertion into a plurality of body orifices, in order to evaluate the anatomy of proximate anatomic structures, to diagnose abnormalities thereof and to treat the diagnosed abnormalities. MRI probes are described that are suitable for use in the mediastinum, in the pancreaticohepaticobiliary system, in the tracheobronchopulmonary system, in the head and neck, in the genitourinary system, the gastrointestinal system, the vascular system, and in the evaluation, diagnosis and treatment of internal fluid collections.

148 Claims, 11 Drawing Sheets

U.S. PATENT DOCUMENTS

| | | | |
|---|---|---|---|
| 4,897,604 A | 1/1990 | Carlson et al. | 324/318 |
| 4,922,204 A | 5/1990 | Duerr et al. | 324/322 |
| 4,932,411 A | 6/1990 | Fritschy et al. | 128/653 |
| 4,960,106 A | 10/1990 | Kubokawa | 128/6 |
| 5,019,075 A | 5/1991 | Spears et al. | 606/7 |
| 5,035,231 A | 7/1991 | Kubokawa et al. | 128/6 |
| 5,050,607 A | 9/1991 | Bradley et al. | 128/653 A |
| 5,090,959 A | 2/1992 | Samson et al. | 604/96 |
| 5,095,911 A | 3/1992 | Pomeranz | 128/662.06 |
| 5,099,208 A | 3/1992 | Fitzpatrick et al. | 324/312 |
| 5,167,233 A | 12/1992 | Eberle et al. | 128/662.06 |
| 5,170,789 A | 12/1992 | Narayan et al. | 128/653.5 |
| 5,190,046 A | 3/1993 | Shturman | 128/662.06 |
| 5,211,165 A | 5/1993 | Dumoulin et al. | 128/653.1 |
| 5,211,166 A | 5/1993 | Sepponen | 128/653.5 |
| 5,217,010 A | 6/1993 | Tsitlik et al. | 128/419 PG |
| 5,260,658 A | 11/1993 | Greim et al. | 324/322 |
| 5,270,485 A | 12/1993 | Jacobsen | 174/15.1 |
| 5,271,400 A | 12/1993 | Dumoulin et al. | 128/653.2 |
| 5,293,872 A | 3/1994 | Alfano et al. | 128/664 |
| 5,294,886 A | 3/1994 | Duerr | 324/318 |
| 5,307,808 A | 5/1994 | Dumoulin et al. | 128/653.2 |
| 5,307,814 A | 5/1994 | Kressel et al. | 128/653.5 |
| 5,318,025 A | 6/1994 | Dumoulin et al. | 128/653.2 |
| 5,347,221 A | 9/1994 | Rubinson | 324/318 |
| 5,348,010 A | 9/1994 | Schnall et al. | 128/653.2 |
| 5,352,979 A | 10/1994 | Conturo | 324/307 |
| 5,355,087 A | 10/1994 | Claiborne et al. | 324/322 |
| 5,358,515 A | 10/1994 | Hüter et al. | 607/101 |
| 5,365,928 A | 11/1994 | Rhinehart et al. | 128/653.5 |
| 5,370,644 A | 12/1994 | Langberg | 606/33 |
| 5,372,138 A | 12/1994 | Crowley et al. | 128/662.06 |
| 5,375,596 A | 12/1994 | Twiss et al. | 128/653.1 |
| 5,400,787 A | 3/1995 | Marandos | 128/653.5 |
| 5,411,476 A | 5/1995 | Abrams et al. | 604/95 |
| 5,413,104 A | 5/1995 | Buijs et al. | 128/653.5 |
| 5,419,325 A | 5/1995 | Dumoulin et al. | 128/653.2 |
| 5,421,338 A | 6/1995 | Crowley et al. | 128/662.06 |
| 5,429,132 A | 7/1995 | Guy et al. | 128/653.1 |
| 5,435,302 A | 7/1995 | Lenkinski et al. | 600/422 |
| 5,437,277 A | 8/1995 | Dumoulin et al. | 128/653.1 |
| 5,439,000 A | 8/1995 | Gunderson et al. | 128/664 |
| 5,443,066 A | 8/1995 | Dumoulin et al. | 128/653.1 |
| 5,443,489 A | 8/1995 | Ben-Haim | 607/115 |
| 5,447,156 A * | 9/1995 | Dumoulin et al. | 128/653.2 |
| 5,451,232 A | 9/1995 | Rhinehart et al. | 606/192 |
| 5,451,774 A | 9/1995 | Jacobsen | 250/227.24 |
| 5,462,055 A | 10/1995 | Casey et al. | 128/653.5 |
| 5,476,095 A | 12/1995 | Schnall et al. | 128/653.2 |
| 5,498,261 A | 3/1996 | Strul | 606/29 |
| 5,507,743 A | 4/1996 | Edwards et al. | 606/41 |
| 5,512,825 A | 4/1996 | Atalar et al. | 324/309 |
| 5,520,644 A | 5/1996 | Imran | 604/95 |
| 5,524,630 A | 6/1996 | Crowley et al. | 128/662.06 |
| 5,540,679 A | 7/1996 | Fram et al. | 606/27 |
| 5,558,093 A | 9/1996 | Pomeranz | 128/660.03 |
| 5,578,008 A | 11/1996 | Hara | 604/96 |
| 5,588,432 A | 12/1996 | Crowley | 128/660.03 |
| 5,598,097 A | 1/1997 | Scholes et al. | 324/316 |
| 5,609,606 A | 3/1997 | O'Boyle | 606/194 |
| 5,611,807 A | 3/1997 | O'Boyle | 606/169 |
| 5,623,241 A | 4/1997 | Minkoff | 335/296 |
| 5,647,361 A | 7/1997 | Damadian | 128/683.2 |
| 5,660,180 A | 8/1997 | Malinowski et al. | 128/660.03 |
| 5,682,897 A | 11/1997 | Pomeranz | 128/662.06 |
| 5,699,801 A | 12/1997 | Atalar et al. | 128/653.2 |
| 5,715,825 A | 2/1998 | Crowley | 128/602.06 |
| 5,728,079 A | 3/1998 | Weber et al. | 604/280 |
| 5,738,632 A | 4/1998 | Karasawa | 600/410 |
| 5,775,338 A | 7/1998 | Hastings | 128/898 |
| 5,792,055 A | 8/1998 | McKinnon | 600/410 |
| 5,833,608 A * | 11/1998 | Acker | 600/409 |
| 5,833,632 A | 11/1998 | Jacobsen et al. | 600/585 |
| 5,840,031 A | 11/1998 | Crowley | 600/440 |
| 5,868,674 A | 2/1999 | Glowinski et al. | 600/410 |
| 5,916,162 A | 6/1999 | Snelten et al. | 600/411 |
| 5,928,145 A | 7/1999 | Ocali et al. | 600/410 |
| 5,938,609 A | 8/1999 | Pomeranz | 600/439 |
| 5,938,692 A | 8/1999 | Rudie | 607/101 |
| 5,964,705 A | 10/1999 | Truwit et al. | 600/423 |
| 5,968,052 A | 10/1999 | Sullivan, III et al. | 606/108 |
| 6,004,269 A | 12/1999 | Crowley et al. | 600/439 |
| 6,011,995 A | 1/2000 | Guglielmi et al. | 607/99 |
| 6,171,240 B1 | 1/2000 | Young et al. | 600/410 |
| 6,019,737 A | 2/2000 | Murata | 600/585 |
| 6,026,316 A | 2/2000 | Kucharczyk et al. | 600/420 |
| 6,031,375 A | 2/2000 | Atalar et al. | 324/307 |
| 6,032,078 A | 2/2000 | Rudie | 607/101 |
| 6,051,974 A | 4/2000 | Reisker et al. | 324/318 |
| 6,058,323 A | 5/2000 | Lemelson | 600/408 |
| 6,061,587 A | 5/2000 | Kurcharczyk et al. | 600/411 |
| 6,078,831 A | 6/2000 | Belef et al. | 600/424 |
| 6,104,943 A | 8/2000 | Frederick et al. | 600/410 |
| 6,263,229 B1 * | 7/2001 | Atalar et al. | 600/423 |
| 6,332,089 B1 | 12/2001 | Acker et al. | 600/424 |

FOREIGN PATENT DOCUMENTS

| | | |
|---|---|---|
| EP | 0 850 595 A1 | 7/1998 |
| EP | 0 908 739 A2 | 4/1999 |
| JP | 6-70902 | 3/1994 |
| WO | WO 98/52064 | 11/1998 |
| WO | WO 98/52461 | 11/1998 |
| WO | WO 99/18852 | 4/1999 |
| WO | WO 99/59479 | 11/1999 |

OTHER PUBLICATIONS

Ladd et al.; "Guidewire Antennas for MR Fluoroscopy", Magnetic Resonance in Medicine, Academic Press, Duluth, MN, US., vol. 37(6): 891–897, (Jun. 1, 1997).

Martin et al.; "An Expandable Intravenous RF Coil For Imaging the Artery Wall", Proceeding of the International Society For Magnetic Resonance In Medicine, Fourth Scientific Meeting and Exhibition, New York, USA Apr. 27–May 3, 1996, vol. 1, page 402.

Quick et al; "Vascular Stents as RF–Antennas for Intravascular MR–Guidance and–Imaging", Proceedings of the International Society for Magnetic Resonance in Medicine, Seventh Scientific Meeting and Exhibition, Philadelphia, Pennsylvania, USA May 22–28, 1999, vol. 1, page 577.

Atalar et al.;"High Resolution Intravascular MRI and MRS using A Catheter Receiver Coil,", Magnetic Resonance in Medicine, 36:596–605 (1996).

Farmer et al.;"Implanted Coil MR Microscopy of RenalPathology", Magn. Reson. Med., 10: 310–323 (1989).

Hoult et al,; " The Signal–to–Noise Ratio of the Nuclear Magnetic Resonance Experiment"J. Magn. Reson. , 24:71–85 (1976).

Hoult; "Rotating Frame Zeugmatography", Phil. Trans. R. Soc. Lond. B. 289:543–547 (1980).

Jolesz et al.; "Interventional Magnetic Resonance Therapy", Seminars in Interventional Radiology, 12: 20–27 (1995).

Ocali et al.;"Intravascular Magnetic Resonance Imaging Using a Loopless Catheter Antenna", MRM, 37:112–118 (1997).

Silverman et al.;"Interactive MR–guided Biopsy in an Open configuration MR Imaging System", Radiology, 197: 175–181 (1995).

* cited by examiner

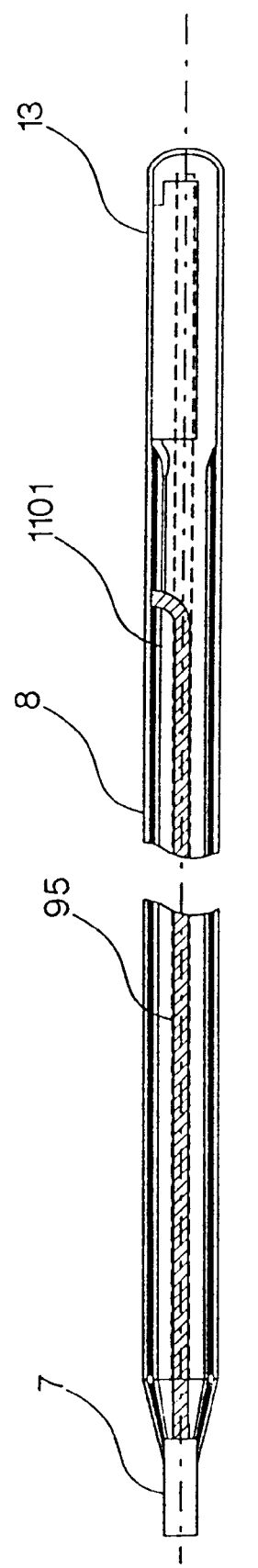
Fig. 11
Fig. 11A

METHODS FOR IN VIVO MAGNETIC RESONANCE IMAGING

REFERENCE TO PRIOR APPLICATIONS

This application claims the benefit of U.S. Provisional Patent Application No. 60/129,368 filed Apr. 15, 1999, U.S. Provisional Patent Application No. 60/129,364, filed Apr. 15, 1999, U.S. Provisional Patent Application No. 60/192,133 filed Mar. 24, 2000, and is a continuation-in-part of U.S. patent application Ser. No. 09/536,090 to Albert C. Lardo et al., filed Mar. 24, 2000, and is also a continuation-in-part of U.S. patent application Ser. No. 09/360,144 to Ocali et al., filed Jul. 26, 1999, which is a continuation-in-part of U.S. patent application Ser. No. 08/638,934 to Ocali et al., filed Apr. 25, 1996, now U.S. Pat. No. 5,928,145, issued Jul. 27, 1999. The disclosures of these applications are incorporated herein by reference.

BACKGROUND OF THE INVENTION

1. Field of the Invention

The invention relates in general to magnetic resonance imaging, and in particular to methods for interventional in vivo magnetic resonance imaging.

2. Related Art

Magnetic resonance imaging (MRI) is a well known, highly useful technique for imaging matter. It has particular use with imaging the human body or other biological tissue without invasive procedures or exposure to the harmful radiation or chemicals present with x-rays or CT scans. MRI uses changes in the angular momentum or "spin" of atomic nuclei of certain elements to show locations of those elements within matter. In an MRI procedure, a subject is usually inserted into an imaging machine that contains a large static magnetic field generally on the order of 0.2 to 4 Tesla although machines with higher and lower strength fields are being developed and used. This static magnetic field tends to cause the vector of the magnetization of the atomic nuclei placed therein to align with the magnetic field. The subject is then exposed to pulses of radio frequency (RF) energy in the form of a second, oscillating, RF magnetic field having a particular frequency referred to in the art as a resonant or Larmor frequency. This frequency is equal to the rate that the spins rotate or precess.

This second field is generally oriented so that its magnetic field is oriented in the transverse plane to that of the static magnetic field and is generally significantly smaller. The second field pulls the net magnetism of the atomic nuclei off the axis of the original magnetic field. As the second magnetic field pulses, it pulls the spins off axis. When it is turned off, the spins "relax" back to their position relative to the initial magnetic field. The rate at which the spins relax is dependent on the molecular level environment. During the relaxation step, the precessing magnetization at the Larmor frequency induces a signal voltage that can be detected by antennas tuned to that frequency. The magnetic resonance signal persists for the time it takes for the spins to relax. Since different tissues have different molecular level environments, the differences in relaxation times provides a mechanism for tissue contrast in MRI. The magnetic resonance signal is detected in the form of a voltage that the precessing magnetization induces in an antenna placed nearby.

In order to image the magnetic resonance signal it is necessary to encode the locations of the resonant spins. This is performed by applying pulses of gradient magnetic fields to the main magnetic field in each of the three dimensions. By creating these fields, the location of resonant nuclei can be determined because the nuclei will resonate at different Larmor frequencies since the magnetic field they experience differs from their neighbors. The magnetic resonance (MR) image is a representation of the magnetic resonance signal on a display in two or three dimensions. This display usually comprises slices taken on an axis of interest in the subject, or slices in any dimension or combination of dimensions, three-dimensional renderings including computer generated three-dimensional "blow-ups" of two-dimensional slices, or any combination of the previous, but can comprise any display known to the art.

MR signals are very weak and therefore the antenna's ability to detect them depends on both its size and its proximity to the source of those signals. In order to improve the signal of an MRI, the antenna may be placed near or inside the subject to be imaged. Such improvements can enable valuable increases in resolution sensitivity and reduction of scan time.

Interventional magnetic resonance antennas and coils have been known and used for in vivo examination of organs, tissue, and other biological structures. See, e.g., U.S. Pat. No. 5,699,801 to Atalar et al. However, such devices are not optimized for clinical utility in transesophageal, transtracheal or transbronchial, transurethral, transrectal, transvaginal, intravascular, and other interventional applications because the probes have undesirable mechanical properties, are of incorrect dimension to be useful in these areas, or have not been specifically designed for use in procedures associated with the areas.

SUMMARY OF THE INVENTION

It is desired in the art to produce systems and methods for evaluation of anatomic areas. Evaluation of an anatomic area may pertain to normal or abnormal features of the anatomic area. Evaluation of an anatomic area may be undertaken simultaneously with other diagnostic procedures, including those interventional procedures that require insertion of a diagnostic tool within the human body, through a naturally occurring or iatrogenically produced orifice. Evaluation of an anatomic area may be undertaken simultaneously with therapeutic interventions, using techniques for therapeutic interventions well-recognized in the art such as biopsies, excisions, ablations, drug deliveries or other types of local or systemically directed treatments.

It is further desired in the art to produce systems and methods for performing medical interventions, where guidance for the interventions can be anatomically detailed and can further include the entire region of anatomic interest. A medical intervention may be a diagnostic or a therapeutic procedure or some combination thereof. As understood herein, any person who views images produced that represent an anatomic area in order to understand that anatomic area may be termed a "diagnostician," even though that person is viewing the images for therapeutic as well as diagnostic purposes, and even if that person is viewing the images only to understand the anatomy and not to diagnose an abnormality.

In certain embodiments, the present invention provides systems and methods for the evaluation of anatomy of the mediastinum, and for diagnosis and treatment of abnormalities therein.

In certain embodiments, the present invention provides systems and methods for the evaluation of the pancreaticohepaticobiliary anatomy, and for diagnosis and treatment of abnormalities therein.

In certain embodiments, the present invention provides systems and methods for the evaluation of the tracheobronchopulmonary anatomy, and for diagnosis and treatment of abnormalities therein.

In certain embodiments, the present invention provides systems and methods for the evaluation of the head and neck anatomy, and for diagnosis and treatment of abnormalities therein.

In certain embodiments, the present invention provides systems and methods for the evaluation of the genitourinary anatomy, and for diagnosis and treatment of abnormalities therein.

In certain embodiments, the present invention provides systems and methods for the evaluation of the vascular anatomy, and for diagnosis and treatment of abnormalities therein.

In certain embodiments, the present invention provides systems and methods for the evaluation of the gastrointestinal system, and for diagnosis and treatment of abnormalities therein.

In certain embodiments, the present invention provides methods for evaluating internal fluid collections, for diagnosing and for treating them.

Other features and advantages of the present invention will become more apparent from the following detailed description, taken in conjunction with the accompanying drawings which illustrate, by way of example, the principles of the invention.

BRIEF DESCRIPTION OF THE DRAWINGS

Objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

FIGS. 11 and 11A show another embodiment of a probe designed for use in the urethra.

DETAILED DESCRIPTION

The invention will now be described with reference to certain illustrated embodiments and certain exemplary practices. Specifically, the invention will be described hereinafter in connection with evaluating an anatomic area, with diagnosing an abnormality of the anatomic area and with treating a diagnosed abnormality thereof. However, it should be understood that the following description is only meant to be illustrative of the invention and is not meant to limit the scope of the invention which is applicable to other forms of anatomic evaluation, diagnosis and treatment, as will be evident to practitioners in the art.

Figure 1:
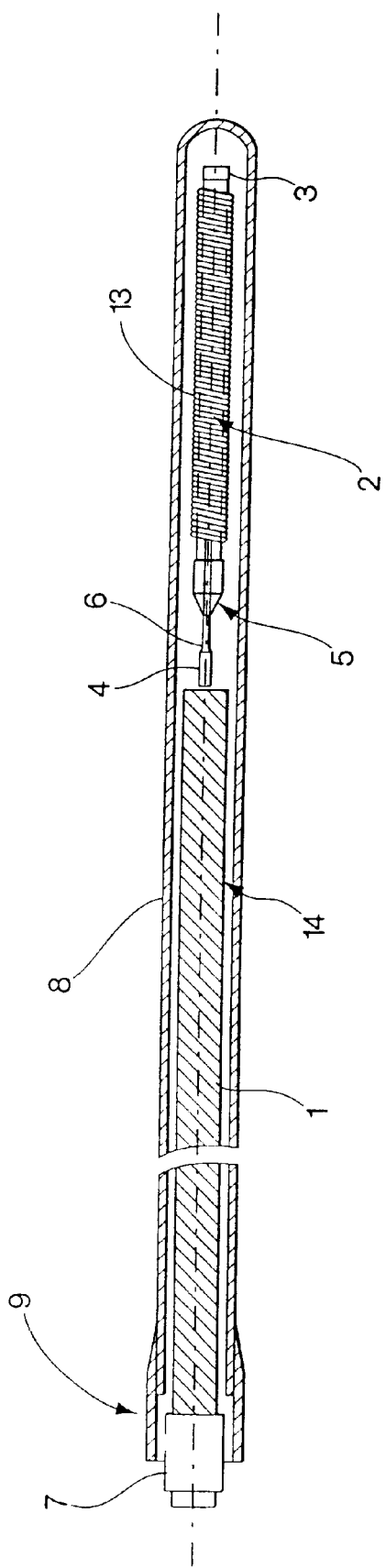
FIG. 1 shows a detailed cross-sectional side view illustrating one embodiment of a probe according to the invention.
Figure 2:
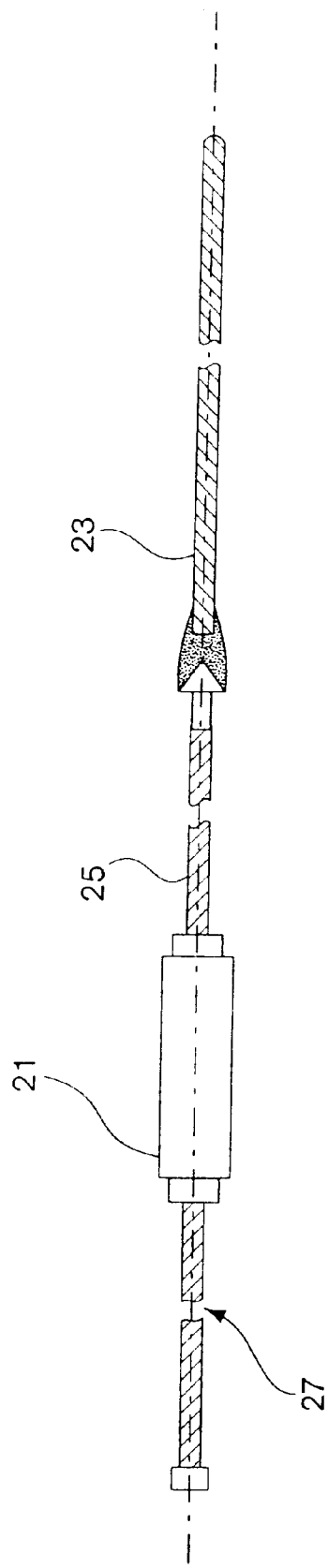
FIG. 2 shows a high-level diagrammatic cross-sectional side view of the probe of the invention according to an embodiment of the present invention.

With reference to FIG. 1, a probe of the invention according to one embodiment comprises an insulating tube 8 (such as, but not limited to, a catheter or a nasogastric tube) encasing a magnetic resonance antenna whip 13 which can comprise a wire 2 coiled around a mandrel 3. The insulating tube 8 shown here is significantly larger than the probe shaft 1 but could be a thin sleeve or coating contoured to follow the shape of the probe. In one embodiment, the insulating tube 8 would have a thickness of 0.005 inches or less. In another embodiment, the probe does not contain the insulating tube. The wire 2 preferably comprises a copper wire having a diameter of 32 AWG, and the mandrel 3 preferably comprises PVDF or Nitinol tubing having a 0.016 inch outer diameter and 0.008 inch inner diameter, +/−0.002 inches. A probe shaft (which can comprise any type of coaxial cable) 1 is operatively connected to the wire 2 for conducting a received signal to a magnetic resonance scanner via a connector 7 and an interface 21 (FIG. 2). The probe shaft 1 preferably has a 50-ohm impedance Teflon dielectric with silver-plated copper as shielding, but such design is not required. The core 4 of the probe shaft 1 preferably extends beyond the sheath 14 and is connected to the coiled wire 2 via a soldering joint 6, whereby the wire 2 acts as a continuation of the core 4. The coiled wire 2 and probe shaft 1 are completely sealed inside the insulating tube 8, thereby isolating them from direct contact with any physiological membrane or fluids. A hub and strain relief can be provided at a proximal end of the insulating tube 8.

FIG. 1 shows only one possible design of probe antenna which could be used with the current inventions. One of skill in the art would recognize that many different antenna designs could be used. In particular, the antenna could be a loop design such as the one depicted in FIG. 7 or could alternatively be any type of relatively linear or slightly bent design of antenna including, but not limited to, any of the designs described or depicted in U.S. patent application Ser. No. 09/536,090 to Lardo et al., filed Mar. 24, 2000. Alternatively, the antenna may be of loop design where the shape of the antenna comprises a loop of wire (or a similar substance) including, but not limited to, a solenoid. The loop design can be a collapsible loop design such as the type described in U.S. Provisional Patent Application No. 60/192,133. Additionally, the probes of the current invention can be inserted through an access structure 81 such as would be known to the art to get the probe inside the body. In FIG. 8 one possible access structure 81 is depicted showing a probe placed inside an access structure 81 such as, but not limited to, a catheter. FIG. 8 further shows a mark 83 which could optionally be placed on the probe to show the proper insertion distance of the probe.

In a first embodiment, the invention provides an endo-esophageal magnetic resonance imaging probe for use in magnetic resonance imaging and analysis of the esophagus and anatomy near the esophagus, e.g., the aorta, coronary arteries, mediastinum, etc., with minimal intervention and with a high level of accuracy. Positioning the probe within the esophagus can delineate the adjacent anatomy while a biopsy or ablation procedure is simultaneously carried out on a designated anatomic structure. For example, a MRI probe positioned within the esophagus may allow the anatomy of the mediastinum to be delineated during the performance of a mediastinoscopy. In this example, the signals produced by the endo-esophageal probe may be used to guide biopsy of mediastinal lymph nodes safely, without impinging upon the major blood vessels in the region. Using the methods of the present invention, endo-esophageal lesions may also be evaluated, diagnosed and treated. Neoplasms, for example, may be diagnosed using MRI signals, so that malignancies are identified at early stages and are distinguished from benign and pre-malignant lesions. Esophageal varices, for example, may be diagnosed, assessed and treated using MRI images obtained according to the present invention.

In certain embodiments of the present invention, anatomy of the mediastinum may be delineated by these systems and methods. Structures within the mediastinum are considered to include those anatomic structures within the anterior, posterior, middle and superior mediastina, as those areas are understood within the medical arts. For example, the middle mediastinum is understood to contain the pericardium and its contents, as well as certain of the great vessels, the tracheal bifurcation, the two mainstem bronchi, and certain bronchial lymph glands. The posterior mediastinum is understood to contain the esophagus, the thoracic duct, the azygos veins and the descending thoracic aorta. The anterior mediastinum contains loose areolar tissue and certain lymphatic tissue. The superior mediastinum, lying above the upper level of the pericardium and behind the manubrium, contains certain great vessels, some lymphatic glands, the trachea, the esophagus, and several nerves. The superior mediastinum may be reached via mediastinoscopy, wherein a small incision is made in the sternal notch and dissection is carried into the tissues behind the manubrium and the sternum to gain access to lymph nodes that may be abnormal and to permit their biopsy. Positioning a MRI probe in the esophagus may yield anatomic information to permit a biopsy of a mediastinal lymph node. Positioning a MRI probe in the superior mediastinum, as through a mediastinoscopy incision or similar incisional access, may permit information about adjacent structures to be obtained. This information may permit, through the same or a different access route, the sampling or the biopsy or the excision of designated structures whose MRI images identify them as abnormal. Placing a MRI probe according to the present invention in areas of the mediastinum, including inside the esophagus, within the pericardium or within the areolar tissue of the anterior or posterior mediastinum, may provide images that can guide other diagnostic or therapeutic procedures, including those performed via other access routes, including endovascular access routes. For example, a procedure involving the coronary arteries may be conducted based on images generated from a MRI probe according to the present invention, wherein the MRI probe is placed within a mediastinal structure. A MRI probe according to the present invention could also guide interventional cardiology procedures from an intraluminal position.

In one embodiment, referencing FIG. 1, the insulator tube 8 may comprise a non-magnetic nasogastric tube which isolates the coil from any direct contact with physiological membranes or fluids. The nasogastric tube used as an insulator tube in this embodiment is preferably a vinyl polymer tubing, e.g., medical-grade PVC, having a Shore D hardness of approximately 60. The nasogastric tube may have an outer diameter of 9 French. The nasogastric tube may be similar to a standard feeding tube which is inserted in the nasal cavity and advanced through the esophagus into the stomach, or a pediatric feeding tube. It is known in the art that standard feeding tubes have apertures at their distal end for fluid exchange. To ensure complete isolation of the imaging cable and coil from fluids and other body materials, the apertures in the standard feeding tube may be sealed off, using a medical grade silicone adhesive, such as those manufactured by Dow Corning or could be reformed (such as by using heat on an appropriately shaped mold) to seal and reshape the tube. This shape is likely to be rounded and atraumatic, but such design is not required. Those of ordinary skill in the art will recognize other particular properties, characteristics and dimensions associated with nasogastric tubes. Other types of nasogastric tubes may be used for the purposes of the present invention, or a nasogastric tube may be expressly produced for these purposes. The length of the probe shaft 1 may be selected so as to be locatable within the esophagus, and in one embodiment is approximately 61 cm.

Insertion of a MRI probe may be performed in a wide range of anatomic areas. For example, in another embodiment, a MRI probe may be inserted into the hepaticobiliary system or the pancreas in order to yield anatomic information about the structures in those areas. Collectively the structures of the liver, gallbladder, bile ducts and pancreas may be referred to as "pancreaticohepaticobiliary" structures. To access these structures, a catheter of appropriate dimensions may be delivered into the region of the stomach or duodenum in closest proximity to the pancreas, for evaluation of the pancreas. Endoscopic retrograde cannulation of the pancreas and other accesses to the pancreaticohepaticobiliary ductal system are well-known in the art; these access routes may be advantageously employed for presenting a MRI probe into the proper anatomic region so that it can be imaged. Images obtained using these techniques may be able to delineate the entire pancreas, or may be able to identify sources of external compression impinging upon the ductal structures with anatomic clarity and high resolution.

In another embodiment, the MRI probe of the present invention may be dimensionally adapted for insertion into an endotracheal or a tracheostomy tube. The MRI probe may be inserted through a non-magnetic catheter directed through the endotracheal or tracheostomy access route, to be directed into the more distal airway for evaluation of lesions therein. The MRI probe may be used in concert with biopsy or ablation tools that are addressing the same lesion. Alternatively, a probe positioned within the airway may be used to delineate the anatomy of adjacent structures to identify abnormalities or to provide guidance for procedures in the adjacent areas. For example, a probe positioned at the carina could provide imaging for biopsies of lymph nodes in the subcarinal area or in the mediastinum more generally. Without the need for imaging optics, a catheter directing a MRI probe according to the present invention could be of smaller diameter to permit less irritating access to the patient's airways and to permit entry into the smaller caliber parts of the bronchial tree. An ultrathin MRI receiver according to these systems and methods may be inserted into the airway to illuminate the surrounding region of the lung, imaging the tissues with near-microscopic resolution, thereby permitting characterization of the tumor type and its response to therapy without the need to damage the tissue with a biopsy and potentially spread a malignancy. A probe according to these systems and methods could also be positioned in the intrapleural space using a standard chest tube that had been inserted for diagnostic or therapeutic purposes, with the probe optionally being protected within a sealed catheter to prevent its contact with body fluids, said sealed catheter being dimensionally adapted for insertion into a standard chest tube system. Those structures including the lungs and the tracheobronchial tree may be referred to herein as tracheobronchopulmonary structures.

Catheters of smaller dimensions can be readily envisioned by practitioners of ordinary skill in the art to permit access into the more remote regions of the nasopharynx system. A nasopharyngeal catheter, for example, can be positioned in the posterior nasal passages or the pharynx to allow anatomic evaluation of adjacent structures using a MRI probe according to the present invention. Positioning the probe sufficiently posteriorly within the nasal cavity could permit assessment of adjacent intracranial lesions, including lesions of the pituitary or the sella. In other embodiments, a probe positioned transnasally may be adapted for evaluating the arterial circle of Willis and related vascular structures for abnormalities, for example congenital or other aneurysms.

Further, the MRI probe of the present invention, appropriately positioned, could be used to evaluate lesions of the proximal aerodigestive system or the thyroid. As an example, these systems and methods may be advantageously used in conjunction with or as a substitute for the panendoscopic evaluation of the nasopharynx performed as part of the diagnostic work-up for an isolated neck nodule. More distal positioning of a catheter in the upper airway could transport a MRI probe according to the present invention to the upper esophagus or to the larynx, for evaluation of lesions therein. Such anatomic diagnosis could be readily combined with biopsy or local ablation of lesions, using techniques familiar to practitioners in the otolaryngological art. Similarly, catheters dimensionally adapted for positioning within the ear canal or the Eustachian tube, permitting anatomic assessment of abnormalities of the middle or inner ear, and further permitting evaluation of adjacent intracranial structures and lesions. These systems and methods may be used advantageously to delineate minute anatomic abnormalities of the ossicles, or anatomic abnormalities along the facial nerve. An MRI probe may be combined with traditional surgical techniques in otolaryngology, such as middle ear reconstruction or facial nerve decompression, to provide finely detailed real time images that can guide surgical interventions.

The anatomic imaging presented by these systems and methods may be combined with a variety of diagnostic and therapeutic interventions, as will be recognized by practitioners of ordinary skill in the arts. Therapeutic interventions may include those procedures performed in internal areas of the head and neck, using instruments such as scopes and probes. In addition, however, these systems and methods may provide information about the extensiveness of various tumors requiring resection and the adequacy of that resection, all in real time. Procedures may be performed using MRI guidance where the MRI probe in the head and neck area may provide real time information about where the tumor is anatomically located and how much of it, within which structures, remains to be removed. The systems and methods of the present invention may be particularly useful in those lesions whose extent is not readily diagnosed, such as basal cell carcinomas. These lesions may follow nerves into the orbit or into the intracranial area, extensions not evident with traditional imaging modalities to the surgeon undertaking the resection. Using these systems and methods, by contrast, a surgeon may be able to determine where the tumor is going, what it involves and how much needs to be resected to obtain clean margins. Other tumors where this information may be useful will be readily apparent to head and neck surgeons. These systems and methods may also be advantageously employed to provide real time information to the resecting surgeon or the surgeon performing a biopsy as to the likely areas of lymph node invasion.

As understood herein, the term "head and neck" will be used to refer collectively to those structures of the ear, nose and throat and proximal aerodigestive system as described above, traditionally falling within the province of otorhinolaryngology. The term "head and neck," as used herein, will further include those structures of the neck such as the thyroid, the parathyroid, the parotid and the cervical lymph nodes, and will include also the extracranial portions of the cranial nerves, including but not limited to the facial nerve, this latter nerve being included from its entry into the internal auditory meatus outward. The term "head and neck, as used herein, will also include those structures of the orbit or of the globe, including the oculomotor muscles and nerves, lacrimal glands and adnexal structures. As used herein, the term "head and neck" will further include those intracranial structures in proximity to the aforesaid head and neck structures. These intracranial structures may include, as examples, the pituitary gland, the pineal gland, the nuclei of various cranial nerves, the intracranial extensions of the cranial nerves, the cerebellopontine angle, the arterial circle of Willis and associated vascular structures, the dura, and the meninges.

In yet another embodiment, the invention provides a transurethral magnetic resonance imaging probe for use in magnetic resonance imaging and analysis of the urethra, prostate, bladder, and anatomies in proximity thereto. In this embodiment, the insulating tube 8 preferably comprises a non-magnetic Foley catheter. Those of ordinary skill in the art will recognize the particular properties, characteristics and dimensions associated with Foley catheters. Positioning the Foley catheter in the bladder will permit insertion of the probe to reach the designated anatomic targets. Using a probe in this manner, for example, the anatomy of the prostate can be delineated and areas of abnormality may be defined. This use of the probe may be combined with biopsy techniques well known in the art to permit sampling of lesions identified thereby. The combination of biopsy techniques with anatomic mapping using the MRI probe according to these systems and methods may facilitate diagnosis or extirpation of lesions when they are at an early stage, possibly at an earlier stage than other diagnostic modalities now extant in the art. It is understood in the art that a critical sign of prostate malignancy is the observation of capsular invasion, which is well shown with MRI. The application of radiotherapy via seed implantation could be guided with MRI, and the response to therapy can be monitored. A transurethral MR coil can be combined with a transrectal MR coil to provide a larger field-of-view image of the prostate than is available with a single coil. Furthermore, using a transurethral catheter to access the bladder may permit insertion of MRI probes according to these systems and methods to diagnose bladder lesions, ideally and possibly at an earlier stage than current techniques, and may furthermore be used to guide biopsies and to direct endovesical therapies.

Transurethral placement of MRI probes according to these systems and methods offers a novel modality for evaluation and treatment of female urinary incontinence. In diagnosing this condition, identifying its cause and guiding anatomically precise treatment, high resolution images of the different layers of the paraurethral tissues would be extremely valuable. It is understood, for example, that a clearly identified disruption in the muscle layers surrounding the urethra may be repaired surgically, but also must be guided by detailed anatomic information about the site of the abnormality. MRI probes provided according to these systems and methods may produce the images that would be useful for planning this therapy and monitoring its success.

Other non-magnetic catheters adapted for placement in the genitourinary system may in like manner be utilized as conduits for positioning the MRI probe according to the systems and methods of the present invention. For example, a ureterostomy catheter placed according to standard urological techniques may permit the introduction of a probe into the ureter or renal pelvis. The probe may provide information about lesions in the surrounding anatomic region to target for biopsy. In another embodiment, positioning a MRI probe within a non-magnetic ureteral catheter can be an ongoing source of anatomic guidance for surgeons performing procedures in the vicinity of the ureter, where damage to the ureter is a constant danger. In alternate embodiments, MRI probes according to the present invention may be positioned within the urinary tract using the variety of percutaneously placed drainage devices, whether catheters, drainage tubes or other means of endourinary access presently known in the art or yet to be devised.

In an additional embodiment, the invention provides a transvaginal magnetic resonance imaging probe for use in magnetic resonance imaging and analysis of the vagina and anatomies in proximity thereto. In this embodiment, the insulator tube 8 preferably comprises a non-magnetic uterine manipulator, e.g., a Homie or Zoomie catheter. Such catheters are described in U.S. Pat. No. 4,430,076, the entire disclosure of which is incorporated herein by reference. Those of ordinary skill in the art will recognize the particular properties, characteristics and dimensions associated with such uterine manipulators. The probe may also have a "C" shape to further aid in navigation. Transvaginal or transcervical endouterine placement may be useful in the diagnosis of neoplasia, in the diagnosis and treatment of endometriosis and in the evaluation of infertility. As an example, these systems and methods may be advantageously applied to the diagnosis and treatment of pelvic disorders resulting in pelvic pain syndromes. Current optical techniques permit imaging of the surface of pelvic structures, while a MRI probe would permit transmural evaluation of the affected organs. Further, a MRI probe according to these systems and methods may be used to direct the ablation of hypertrophied tissues and to monitor local tissue responses to treatment. As a further example, MRI probes according to these systems and methods may be employed to diagnose cervical and uterine malignancies and to determine their stages. MRI images can identify the extent of tumor invasion so that appropriate therapy can be selected. Implantation of radiation seeds may be performed to treat certain tumors; these may be positioned within a lesion using the images produced by the MR coils of the present invention. As another example, the systems and methods of the present invention may permit more detailed diagnosis of anatomic abnormalities contributing to infertility such as inflammation-induced scarring or obstruction of the fallopian tubes; these systems and methods may further be combined with therapeutic interventions intended to correct the identified abnormalities. Furthermore, the transvaginal or transcervical placement of MRI probes may be advantageously combined with other techniques useful in treatment of infertility, such as ovum harvest or embryo placement or manipulation. Other uses for this embodiment will be apparent to practitioners of ordinary skill in the art. Uses may be envisioned, for example, in diagnosis of various obstetric conditions where the competence of the cervix needs to be determined or the position of the placenta needs to be identified. With appropriate dimensional modifications, a system according to the present invention may be adapted for other obstetric needs, permitting anatomic evaluation of mother and fetus using transvaginal probes as described herein.

As used herein, the term "genitourinary" shall include those structures of the urinary tract, the male genital system and the female genital system. The urinary tract structures include the urethra, the bladder, the ureters, the kidney and related neural, vascular, lymphatic and adnexal structures. The male genital tract includes the prostate, the seminal vesicles, the testicles, the epididymis and related neural, vascular, lymphatic, ductal and adnexal structures. The female genital tract includes the vagina, the cervix, the non-gravid and gravid uterus, the fallopian tubes, the ovaries, the ova, the fertilized egg, the embryo and the fetus. The term "genitourinary" further refers to those pelvic structures that surround or support the abovementioned structures, such as the paraurethral tissues, the urogenital diaphragm or the musculature of the pelvic floor.

In another embodiment, a MRI probe according to these systems and methods can be positioned within the rectum or colon by the transrectal route. A catheter of appropriate dimensions can be inserted through the anus to a level within the rectum, sigmoid or descending colon where the designated anatomy can be visualized. For example, this approach may be used to delineate the anatomy of the prostate gland, and may further guide the biopsy or the extirpation of lesions undertaken transrectally or transurethrally. As another example, a diagnostic probe using a MRI probe within a fine caliber non-magnetic catheter may be advanced to the level of a known neoplasm to permit determination of the extent of the lesion; such information can be used for staging and may provide the indication for preoperative chemotherapy or radiation.

In one embodiment, the systems and methods of the present invention may be used for the evaluation, diagnosis or treatment of a structure in the gastrointestinal system, or for the evaluation, diagnosis or treatment of a region of the gastrointestinal anatomy. As used herein, the term "gastrointestinal" shall include structures of the digestive system including the esophagus, the stomach, the duodenum, jejunum and ileum (small intestine), the appendix and the colon. The term "gastrointestinal anatomy" shall refer to the structures of the gastrointestinal system as well as the surrounding supporting structures such as the mesentery and the enclosing structures such as the peritoneum, the diaphragm and the retroperitoneum. Disorders of the gastrointestinal system are well-known in the medical arts, as are disorders of the gastrointestinal anatomy. Diagnostic or therapeutic interventions into these areas using the systems and methods of the present invention may take place using access structures familiar to skilled artisans, such as endoscopes, laparoscopes, tubes, catheters, needles, cannulae, or any other access structure, whether used for other purposes or whether specifically fabricated to provide access to the structures of the gastrointestinal system or to regions of the gastrointestinal anatomy. In an exemplary embodiment, a MRI probe according to these systems and methods may be passed into the stomach using a conventional endoscope, using a conventional nasogastric tube as an access structure or using a modified nasogastric tube as an insulating tube, as previously described. According to these systems and methods, a MRI probe may be passed into the gastrointestinal system or into any other system through an access structure to gain access thereto, or the MRI probe may be insulated from body contact within an insulating tube, said insulating tube to be passed into the target structure either by passage through an access structure or by passage into the target structure without an access structure. These principles, well-exemplified by embodiments directed to the gastrointestinal system, apply for using these systems and methods in any anatomic region of the body or in any anatomic structure.

In one embodiment, the systems and methods of the present invention may be used for the evaluation, diagnosis and treatment of the vascular system. The vascular system is understood to include the blood vessels of the body, both arterial and venous. The vascular system includes both normal and abnormal blood vessels, named and unnamed vessels, and neovascularization. Access to the vascular system takes place using techniques familiar to practitioners of ordinary skill in the art. Positioning a MRI probe in the vascular system may be used in combination with other techniques for vascular evaluation, diagnosis and therapy, as would be well-known to skilled artisans. The present invention may be used in blood vessels of all sizes, limited only by the dimensional specifications required in order to fabricate the MRI probe, as disclosed herein. Hence, with appropriate miniaturization as would be familiar to one of ordinary skill in the art, using for example, miniaturization techniques such as printed flexible circuits, a MRI probe according to the present invention may be dimensionally adapted to enter smaller caliber vessels, such as those comprising the distal coronary circulation, the intracranial circulation, the circulation of the distal extremities or the distal circulation of the abdominal viscera. As techniques for miniaturization evolve in the art, it is understood that these techniques may be readily applied to the systems and methods as disclosed herein, without departing from the scope of the present invention. According to these systems and methods, furthermore, positioning a MRI probe within the vascular system may be useful for evaluating, diagnosing and treating conditions in structures adjacent to or in proximity to the particular vessel within which the probe is situated. Such structures are termed "perivascular structures." As an example, a probe placed within a vessel feeding a neoplasm may provide information about the vasculature specific to the neoplasm and may further provide information about the neoplasm itself. The probe may then be used to guide other therapeutic modalities directed to the neoplasm itself, with those modalities approaching the neoplasm either via an intravascular approach or via an extravascular approach. As another example, a MRI probe placed within a coronary artery may provide information about the vessel itself and about the myocardium that is perfused by the vessel or that is adjacent to the vessel. A probe thus positioned may be able to guide therapeutic interventions directed to the myocardial tissue, and may also be able to guide endovascular or extravascular manipulations directed to the vessel itself. It will be readily appreciated by those of ordinary skill in the art that a number of other applications exist or may be discovered with no more than routine experimentation using the systems and methods of the present invention within the vascular system.

It is understood that access to anatomic structures using the systems and methods of the present invention may be provided via naturally occurring anatomic orifices, as indicated in the examples above. It is further understood, however, that access to anatomic structures using these systems and methods may be additionally provided using temporary or permanent orifices that have been created medically. For example, a non-magnetic t-tube or other endobiliary tube put in place with surgical methods or during interventional radiology may provide an access route for a catheter bearing a MRI probe according to the present invention to be inserted for evaluation of the relevant anatomy. As another example, a drainage catheter placed surgically or radiologically to drain a cyst, a pseudocyst or a fluid collection may provide an access route for a catheter bearing a MRI probe to be inserted to evaluate the relevant anatomy, a feature that is particularly advantageous for the diagnosis and treatment of unusual anatomic arrangements that may be giving rise to the cyst, pseudocyst or fluid collection. In certain embodiments, a drainage catheter or other access structure may be used for draining the cyst, pseudocyst or fluid collection or for injecting an agent into the cyst, pseudocyst or fluid collection, thereby to treat it or thereby to delineate its anatomy better, e.g., by using a contrast agent or a vital dye like Methylene Blue. Other examples where an iatrogenic orifice may be employed to provide access for a MRI probe according to the present invention will be readily apparent to those of ordinary skill in the arts. As used herein, the term "access structure" may be applied to any tube, conduit, catheter, stoma, cannula or other medical device suitable for allowing a MRI probe to be inserted into a subject's body, thereby to gain access to a body area or a body tissue of interest. An access structure may be left in place while a MRI probe is used to evaluate an anatomic area, or an access structure may be removed, so that the MRI probe is left in situ without an access structure in place. As an example of this latter situation, an access structure such as a non-magnetic needle or a cannula may be used to gain entry into an anatomic area such as an internal cyst, fluid collection or pseudocyst. The MRI probe may be placed through the needle to be positioned within the targeted area. The needle or cannula may be used to withdraw fluid from the targeted area for diagnosis or for treatment; after fluid removal, the needle or cannula may be withdrawn, leaving the MRI probe in its preselected position, from which signals may be obtained to delineate any anatomic abnormalities in the area after fluid removal. This technique may be used, with appropriate dimensional modifications, for example, to diagnose the presence of a breast cancer in juxtaposition to a breast cyst.

Probe systems according to the present invention may further be employed in conjunction with traditional endoscopic procedures or as a replacement for optical endoscopies. An MRI probe may be inserted in combination with a standard (non-magnetic) cystoscope, for example, or as a substitute for optical cystoscopy. Alternatively, an optical cystoscopy could be performed, followed or preceded by a MRI evaluation using the present invention. These systems and methods may also be adapted for use in conjunction with endoscopic surgical procedures such as laparoscopies, where the MRI image would be used as a substitute for or an adjunct to optical methods. The image produced using MRI is also available for digital enhancement and manipulation, so that image quality can be improved and more precise anatomic data can be obtained. Further, MRI data can be processed to produce digital coordinates that may be used to guide robotic or other telesurgical interventions. In certain contexts, MRI guidance may prove superior to conventional optical technologies. For example, the biopsy of retroperitoneal lymph nodes may be advantageously guided using MRI probes according to the present invention, where the MRI images can identify pathological lymph nodes and their extent, and can further readily distinguish between lymph nodes and surrounding anatomic structures. Positioning a MRI probe according to the present invention can take place using a catheter that may be placed in a relatively inaccessible anatomic space such as the axilla or inguinal area, to permit identification of abnormal lymph nodes therein and further to permit their diagnosis using imaging, image-guided biopsy or both. Techniques to open up a space surrounding a catheter can be directed by images produced by the MR probe to direct the probe and any associated biopsy device efficiently towards the target lesion.

With appropriate dimensional modification of the MRI system, probes according to the present invention may be utilized during conventional surgical procedures to provide information about adequacy of extirpation or about the surgeon's proximity to various structures rendered inaccessible to direct vision. For example, during complex pelvic procedures, it is imperative to protect the ureters from damage. Positioning a MRI probe within the ureter may provide the surgeon with important information about the location of the structure and about the proximity of dissection thereto. As another example, in the extirpation of an extensive head and neck tumor, an appropriately positioned MR probe can yield anatomic information about the extent of extirpation and the impingement of the lesion upon adjacent structures. Other examples may be readily envisioned by those of ordinary skill in the arts.

The aforesaid embodiments are understood to be exemplary only. Other embodiments wherein MRI probes may be used within body areas such as body canals, cavities, lumens, passageways, actual or potential spaces will be apparent to practitioners of ordinary skill in the relevant arts. As exemplified herein, a variety of access structures may be used to permit the insertion of MRI probes into the body; while access structures such as catheters, endoscopes, anuscopes, chest tubes, drainage tubes, tracheostomy tubes, introducers and cannulae have been described, other access structures are familiar to practitioners in these arts. Probes sealed within sterile catheters may be used to penetrate and evaluate areas where asepsis is essential, such as the various body interiors.

With appropriate dimensional modifications, probes according to these systems and methods may be adapted for insertion into any body area. Use in the central nervous system, for example, may require fabrication of probes that can be inserted within a sheath through a burr hole or other cranial aperture, or that can be inserted and directed over long distances after intrathecal insertion. Routine experimentation, familiar to practitioners in the art, will permit adaptation of these systems and methods to a range of anatomic locations. Use of these systems and methods in this plurality of anatomic locations, therefore, is understood to fall within the scope of the present invention. Further, practitioners will be able to envision situations where more than one probe assembly according to these systems and methods may be advantageously employed. A plurality of probe assemblies, for example a loopless and a looped antenna, may be combined in a single probe to insert in a single anatomic area. In addition, separate probe assemblies may be used simultaneously, each to be inserted into a particular anatomic area, so that a combined signal is obtained, better to delineate features of the anatomic area. As an example, input from a transurethral and a transrectal probe may be combined to provide more extensive anatomic information about the prostate and surrounding structures. Or, as another example, an endovesical and an endovaginal probe may together provide useful anatomic information about a set of endopelvic structures, or about a structural abnormality leading to incontinence. Other probe combinations can be arranged by practitioners using no more than routine experimentation. As understood herein, an area of anatomic interest may include any part of a subject's body or any body tissue. The examples of areas of anatomic interest that have been provided, therefore, are intended to be illustrative only, with other areas of anatomic interest being readily identifiable by practitioners of ordinary skill in the art. In particular, it will be understood that the aforesaid probe systems and methods for specific preferred embodiments of anatomical applications may incorporate either or both loop antenna or loopless antenna configurations with specific probe geometries and properties for the procedures described. These antenna configurations can be of any type known to the art including, but not limited to, those described in U.S. Pat. No. 5,699,801 to Atalar et al.; U.S. patent application Ser. No. 09/536,090 to Lardo et al., filed Mar. 24, 2000; Atalar E, Bottomley, P A, Ocalio, Correia L L, Kelemen M D, Lima J A, Zerhouri E A "High resolution intravascular MRI and MRS by using a catheter receiver coil" *Magn Reson Med* October 1996; 36(4): 596–605; and Ocalio, Atalar E. "Intravascular magnetic resonance imaging using a loopless catheter antenna" *Magn Reson Med* 1997; 37:112–118 all of which are herein incorporated by reference.

Probe dimensions suitable for various anatomic locations based on some of the uses as described above are provided in Table 1. The antenna lengths given in this table are valid for its use in about 1.5 T magnets or Larmor frequencies of about 64 MHz and generally scale inversely with increasing magnetic field strength as would be understood by one of skill in the art. This table lists types of the applications as discussed above along with some preferred designs for the style of antenna used on the probe. It then lists a recommended internal diameter range and preferred internal diameter. This internal diameter refers to the diameter of the probe within the insulator tube as depicted in FIG. 1. There is also a recommended outer diameter range and preferred outer diameter. This outer diameter refers to the diameter of the insulator tube as depicted in FIG. 1. There are recommended probe length ranges and preferred probe lengths relating to the size of the probe depicted in FIG. 1, and finally recommended and preferred antenna lengths for the different types of applications. In the table, antenna length refers to the length of the antenna 13 whether the whip of loopless antennas, or the length of the coil of loop antennas such as the one depicted in FIG. 7. This table is by no means exhaustive, and other lengths could potentially be used. These dimensions have been chosen as generally more desirable for the performance of more common procedures in these areas, not because they are the only dimensions available.

Figure 6:
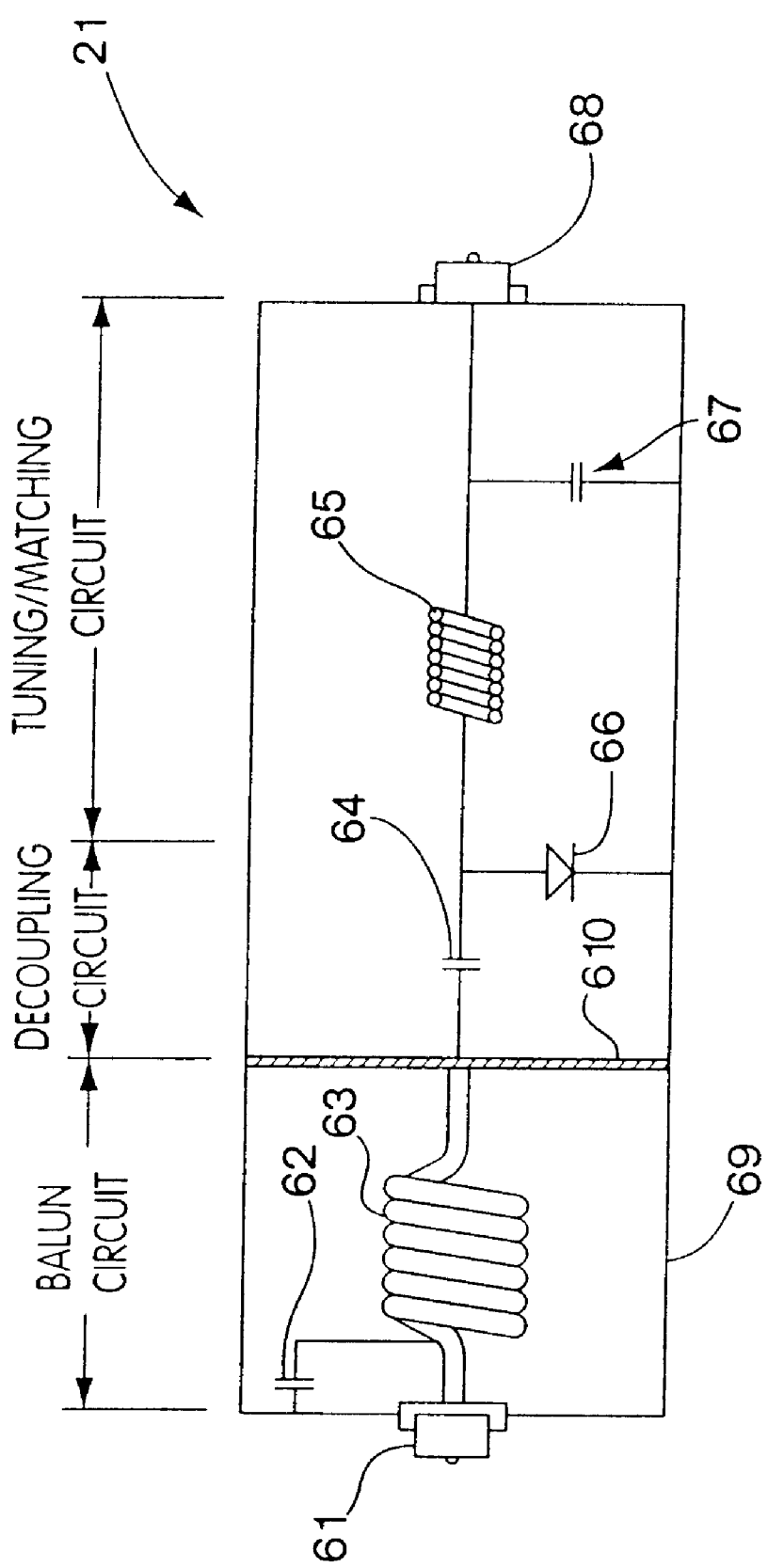
FIG. 6 shows a schematic diagram illustrating details of the interface circuit 21 for loopless antenna circuits of the invention.

FIG. 2 shows a high-level diagrammatic cross-sectional side view of the probe assembly of the invention according to a preferred embodiment, including an antenna that can be encased in a catheter 23, a connecting coaxial cable 25, an interface 21, and a third coaxial cable 27 connecting the probe to the surface coil port of a magnetic resonance scanner. The interface 21 includes, e.g., a balun and decoupling and tuning/matching components. Further details of the interface 21 are shown in FIG. 6 and discussed below with reference thereto.

Figure 3:
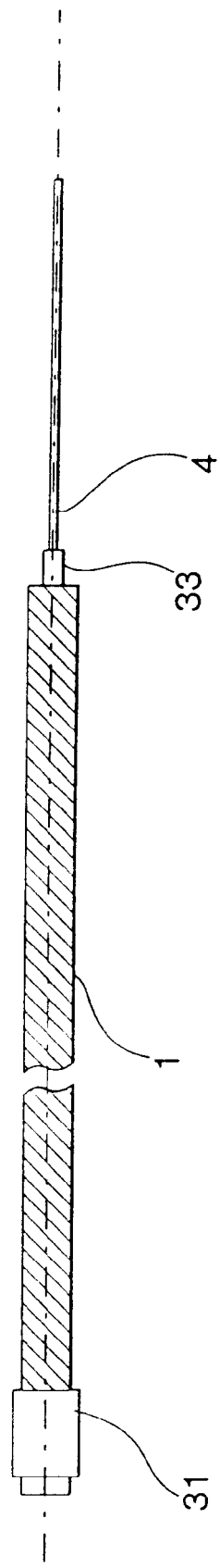
FIG. 3 shows a cross-sectional side view of the coaxial cable assembly of the invention.

FIG. 3 shows a cross-sectional side view of one embodiment of the probe shaft 1. The probe shaft can 1 comprise a conductor core 4 sandwiched concentrically in layers of insulation/dielectric, conductive shielding, and dielectric/insulation, respectively. The preferred embodiment is of the "loopless" antenna type wherein such probe shaft 1 has its top layers of insulation and shielding removed at a distal end 33 and its central conductor core 4 exposed. The exposed central conductor 4 is then insulated with an ultra-thin layer of insulation and may be fabricated from gold-plated Nitinol. The central conductor 4 then acts as an imaging pole or imaging coil of the antenna. The central conductor 4 is optimized by varying its length according to the wavelength and frequency of the signals of interest. The length of the central conductor 4 is approximately 0.25 times this wavelength, but this relationship is more accurately described by a complex function of several parameters, including dielectric constant, wavelength and frequency as described in U.S. patent application Ser. No. 09/536,090 to Lardo et al., filed Mar. 24, 2000. The central conductor 4 may be coiled or may be straight, depending on the application. A connector 31 (such as a BNC connector) can be attached to the proximal end of the coaxial cable for connection to a preamplifier. In an embodiment, the probe shaft 1 may have a length of about 61.0 cm+/−0.1 cm.

The function of the loopless antenna can be described as follows. The coil and the shielding of the coaxial cable form a closed loop and RD signals generated are collected by the loop. These signals are transmitted to the scanner via the coaxial cable. For optimal performance, the input impedance of the coils should be matched with the characteristic impedance of the coaxial cable. The noise resistance of the coil is approximately 20–100 ohms.

Figure 4:
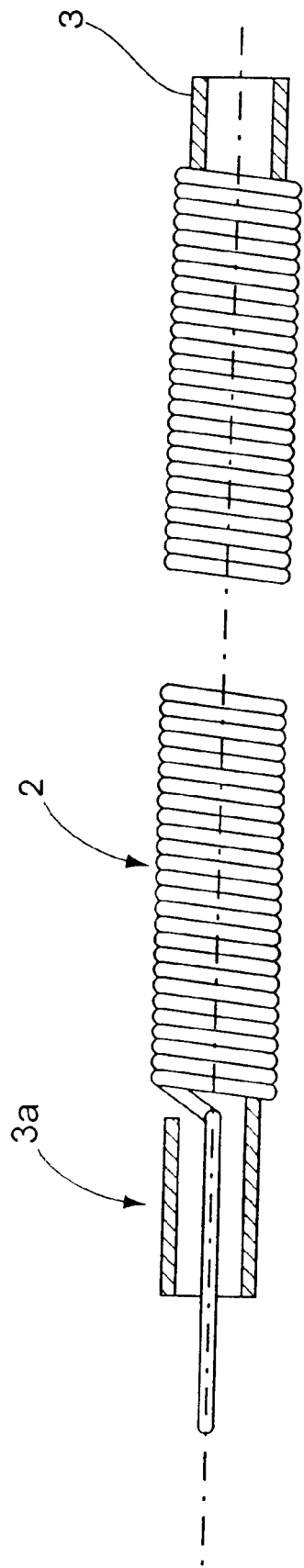
FIG. 4 shows a cross-sectional side view illustrating details of the coil loop assembly of the invention prior to its attachment to the coax cable.

FIG. 4 shows a cross-sectional side view illustrating details of one embodiment of the coil loopless assembly of the invention prior to its attachment to the coax cable. The assembly includes the wire 2 coiled around the mandrel 3 in the configuration and dimensions as shown. In an embodiment, a portion 3a of the mandrel 3 may have a length of about 1.5 cm+/−0.1 cm. In an embodiment, the wire 2 can have a coil length of about 9.4 cm+/−0.1 cm. In an embodiment, the mandrel 3 can have a length of about 14.0 cm+/1 1.0 cm.

Figure 5:
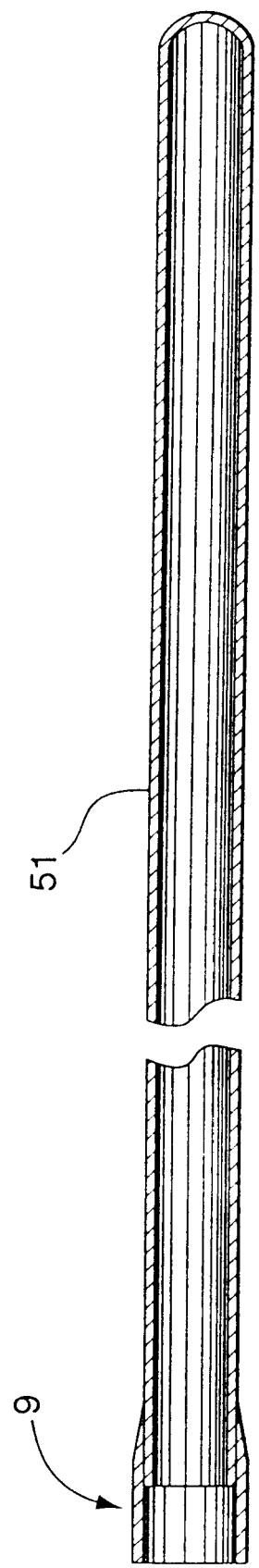
FIG. 5 shows a cross-sectional side view illustrating the typical shape and dimensions of a nasogastric tube used in the invention according to an embodiment of the present invention.

FIG. 5 shows the typical shape and dimensions of a nasogastric tube 51 used in one embodiment of the invention, as discussed above in detail. In an embodiment, the nasogastric tube 51 can have a length of about 40+/−1 inches. In an embodiment, the tube 51 can have an outer diameter of about 0.101 inches. In an embodiment, the tube 51 can have an inner diameter of about 0.060 inches. In an embodiment, the tube 51 may include PVC. In an embodiment, the tube 51 may be sealed off at the distal end.

FIG. 6 shows details of the interface circuit 21 for an antenna circuit of the invention. The interface circuit 21 comprises a balun circuit, a decoupling circuit, and a tuning/matching circuit. The balun circuit is provided for preventing unbalanced current from being induced in the scanner, and includes a rigid coaxial cable inductor coil 63 and a capacitor 62 connecting the ground to a housing 69. The decoupling circuit is provided for selecting the antenna of the invention for MRI detection and for limiting current flow in the antenna when magnetic resonance is not being detected, and includes a decoupling capacitor 64 and a diode 66. A DC current signal generated by the scanner activates the diode, which in turn grounds the DC current, thereby preventing current flow in the coil. However, for normal magnetic resonance detection, the diode is not active and the circuit functions normally. The tuning/matching circuit is provided for matching the impedance of the antenna to the cable and preamplifier input, and includes a tuning/matching capacitor 67 and an inductor 65 in parallel to match the output impedance of the circuit to approximately 50 ohms, which is the input impedance typically required by the preamplifier of a scanner for optimum performance. The specific values of the capacitors 61, 62, 64 and the inductor 65 may be determined in accordance with the specific application by those skilled in the art. A copper plate 610 is provided for isolating the balun from the tuning and matching circuits. A ground-isolated connector 61 and a connector 68 (which can be BNC connectors) can be provided for connecting the interface to coaxial cables 25 and 27 shown in FIG. 2.

The coil antenna of the invention is typically connected to the surface coil or auxiliary coil port of the MRI scanner, and can be used in conjunction with other external receiver coils, e.g., surface coils, etc. In use, MRI signals are excited by the scanner's transmitter coil. The decoupling circuit in FIG. 6 substantially eliminates induced current in the coil of the invention during excitation. In embodiments wherein the balun, tuning/matching and decoupling circuit are proximally located on the probe, these elements preferably remain outside the body during the examination. The signals received by the coil are then transmitted through interface circuitry to a magnetic resonance scanner or other magnetic resonance signal processing device. For example, the signals received by the coil may be transmitted to a GE Signa scanner via that scanner's surface coil or auxiliary coil port.

Figure 7:
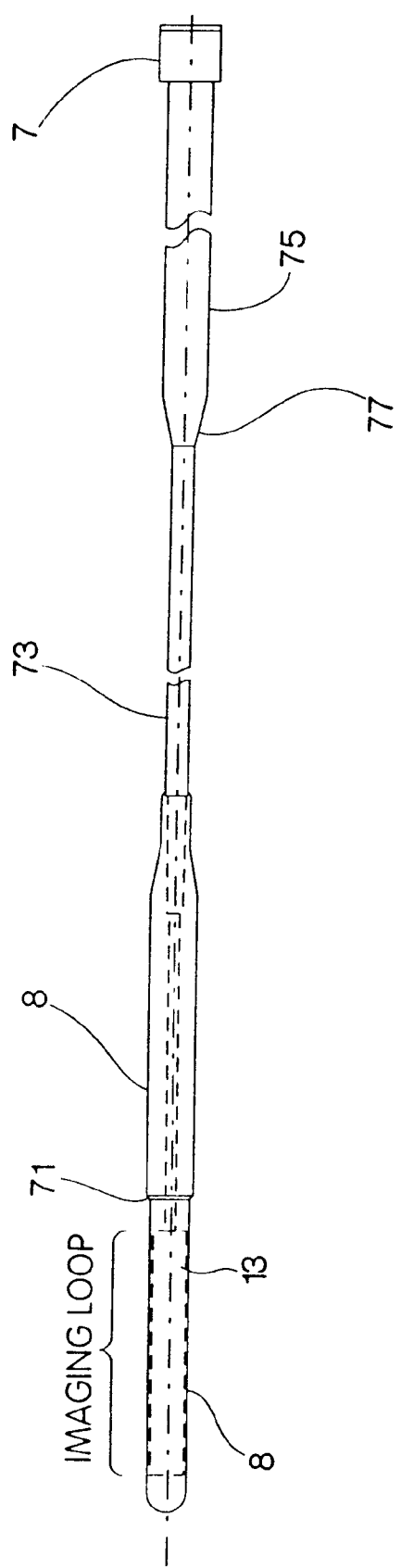
FIG. 7 shows a schematic side view illustrating an embodiment of the invention employing a loop antenna imaging coil. This particular probe is one embodiment of a probe for use in the urethra.
Figure 8:
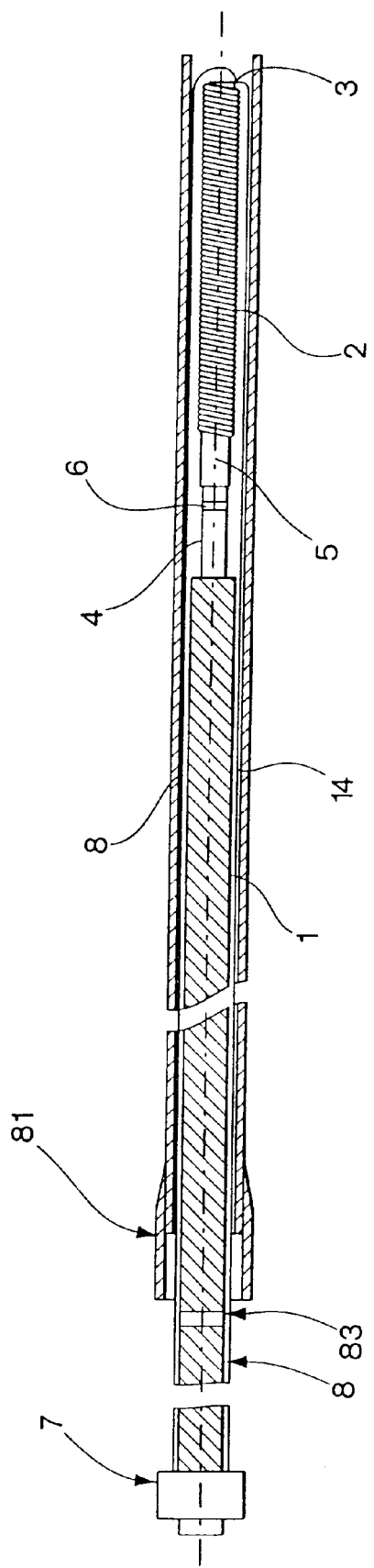
FIG. 8 shows a cross-sectional side view of a probe of the invention within an access structure such a catheter.

FIG. 7 shows a schematic side view illustrating an embodiment of the invention employing a loop antenna imaging coil. This design also provides a reference point 71 where the type of shielding can change a coaxial cable 73 a triaxial balun 75 and a meeting point 77 between the coaxial cable 73 and the triaxial balun 77.

The elongated loop 13 shown in FIG. 7 can comprise two parallel wires shortened at one end. The wires can be made flexible while keeping the separation of the wires constant. Two or more capacitors can be used for tuning and matching as is known in the art. The number of capacitors increases the quality factor (Q) (increases and therefore the signal-to-noise ratio performance of the coil). A shunt diode of the coaxial cable 73 can be used as a decoupling circuit. The circuit eliminates the induced currents on the wire which results in a uniform flip angle and RF excitation of the object of interest. A balun circuit can be used to reduce/eliminate the unbalanced currents on the shield or on the coil. This can result in an increase in signal-to-noise ratio performance of the coil and can also decrease the risk of excessive heating.

Figure 9:
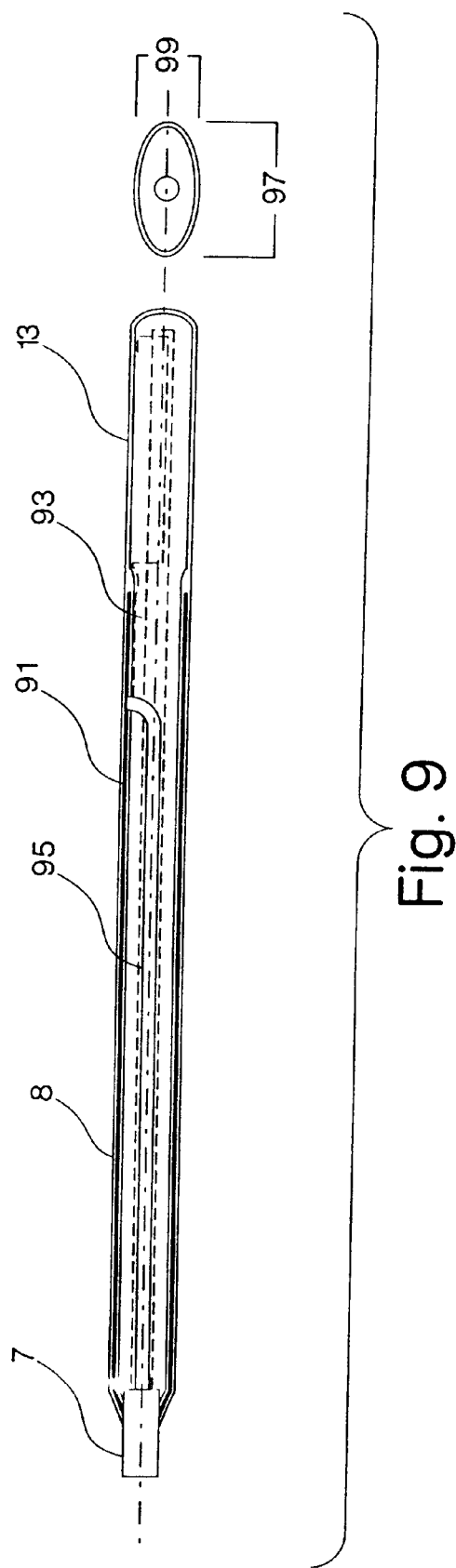
FIG. 9 shows a probe designed for rectal use, for example, as to examine the prostrate. This particular embodiment has an elliptical shape.

FIG. 9 shows one embodiment of a probe designed for use in the rectum. The probe design is similar to other probe designs herein disclosed. The antenna 13 here depicted is a flexible circuit antenna such as the one depicted in FIG. 10. The probe also comprises a coaxial cable 95 and interior shielding 93 and a balun shielding 91. The probe is elliptical in shape having a width 97 greater than its height 99.

Figure 10:
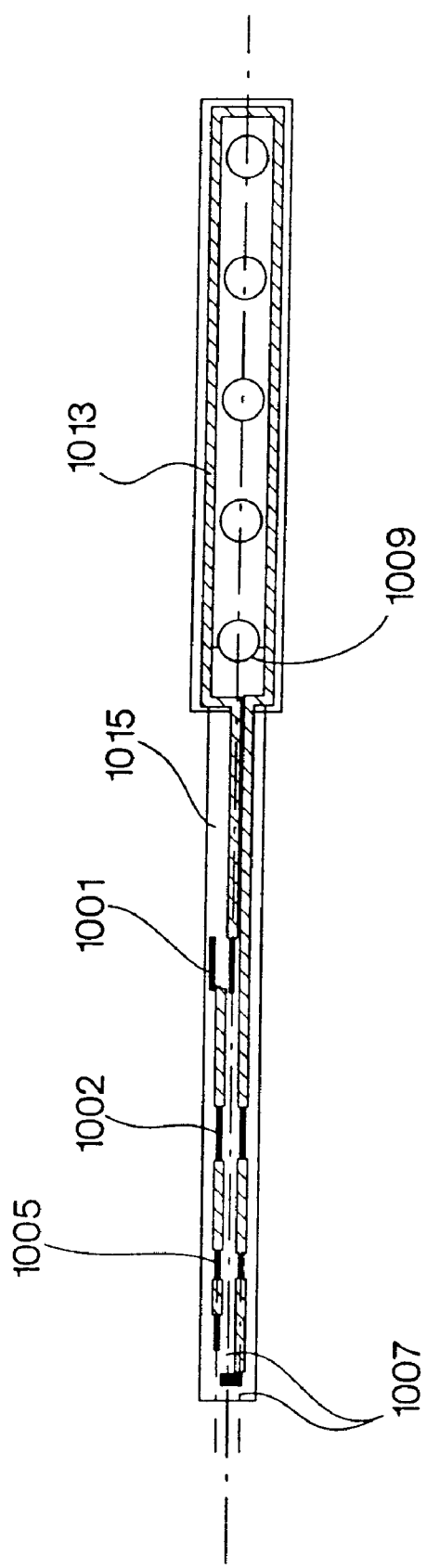
FIG. 10 shows a flexible printed circuit board with a loop etched on the surface which could comprise a loop antenna design for use with the instant invention.

FIG. 10 shows one embodiment of a flex circuit that can comprise the antenna 13 in the invention. Here the loop 1013 is etched onto a circuit board 1015 or similar substance. The circuit board 1015 can comprise holes 1009 for flexibility and can further incorporate circuitry such as parallel capacitors 1002, series capacitors 1001, and a diode 1005. The flex circuit is also likely to have a connective structure 1007 enabling connection to a coaxial cable (such as 95 in FIG. 9) or another type of connection as is known to the art.

FIGS. 11 and 11A show a further embodiment of the probe of the instant invention designed for use in the urethra. This probe comprises a brading or balun sleeve 1101 as shielding.

Although certain embodiments of these systems and methods are disclosed herein, it should be understood that other embodiments are envisioned as would be understood by one of ordinary skill in the art. Although the invention has been described by reference to specific embodiments thereof, it is not intended that the invention be limited to those illustrative embodiments. Rather, it is intended that all variations and modifications as fall within the spirit of the invention be included within the scope of the following claims. Accordingly, no limitation of the invention is intended by the foregoing description and accompanying drawings, except as is set forth in the appended claims.

TABLE 1

| Type of Application (preferred antenna) | Internal Diameter Range | Outer Diameter Range | Preferred Internal Diameter | Preferred Outer Diameter | Probe Length Range | Preferred Probe Length | Antenna Length Range | Preferred Antenna Length |
|---|---|---|---|---|---|---|---|---|
| Esophageal | About 0.5–25 French | About 3–30 French | About 3 French | About 9 French | About 50–150 Centimeters | About 75 Centimeters | About 2–30 Centimeters | About 10 Centimeters |
| Transrectal - including Colon Imaging | About 0.5–55 French | About 2–60 French | About 9 French | About 15 French | About 5–150 Centimeters | About 20–70 Centimeters | About 1–30 Centimeters | About 5–10 Centimeters |
| Prostrate Imaging | About 0.5–9 French | About 2–10 French | About 4 French | About 10 French | About 30–150 Centimeters | About 20–70 Centimeters | About 1–20 Centimeters | About 5–10 Centimeters |
| Transvaginal - Including Vaginal, Cervical, and Uterine Imaging | About 0.5–55 French | About 3–60 French | About 3 French | About 9–14 French | About 20–50 Centimeters | About 30–35 Centimeters | About 1–30 Centimeters | About 20 Centimeters |
| Gastrointestinal Tract-Deep Abdominal and Bioasogastric | | About 1–2.5 French | | About 1/3 Inch | About 50-300 Centimeters | About 150 Centimeters | About 1–30 Centimeters | About 2–10 Centimeters |
| Gastrointestinal Tract-Deep Abdominal and Bioasogastric (large) | | About 10–20 French | | About 15–17 French | About 50–300 Centimeters (or as long as an endoscope) | About 100 Centimeters | About 1–20 Centimeters | About 2–10 Centimeters |
| Transurethral - Including Urinary Incontinence | About 6–10 French | About 13–17 French | About 9 French | About 13 French | About 5–30 Centimeters | About 10 Centimeters | About 2–30 Centimeters | About 5–10 Centimeters |
| Intravascular or Fallopian Guidewire | | About 1–6 French | About 3 French | About 1–3 French | About 80–300 Centimeters | About 100–150 Centimeters | About 2–30 Centimeters | About 10–20 Centimeters |

What is claimed is:

1. A method of performing a medical intervention, comprising:
   providing a MRI probe adapted for insertion into a region of anatomic interest;
   providing an access structure through which the MRI probe may be passed to allow said MRI probe to approach the region of anatomic interest;
   advancing the MRI probe through the access structure toward the region of anatomic interest;
   obtaining magnetic resonance imaging signals from the MRI probe; and
   interpreting the magnetic resonance imaging signals, thereby to guide the medical intervention.

2. A method for evaluating mediastinal anatomy, comprising:
   providing a MRI probe adapted for insertion into an esophagus;
   inserting the MRI probe into the esophagus; and
   obtaining from the MRI probe signals related to anatomy of a mediastinum;
   wherein said MRI probe has a diameter in the range of about 0.5 to 5 French and a length in the range of about 50 to 150 centimeters.

3. The method of claim 2, further comprising using the MRI probe signals to identify a vascular structure of the mediastinum.

4. The method of claim 2, further comprising using the MRI probe signals to identify a lymph node in the mediastinum.

5. The method of claim 2 wherein said MRI probe has a diameter of about 3 French.

6. The method of claim 2 wherein said MRI probe has a length of about 75 centimeters.

7. The method of claim 2 wherein said MRI probe comprises an antenna.

8. The method of claim 7 wherein said antenna has an electrical length in the range of about 2 to 15 centimeters.

9. The method of claim 7 wherein said antenna has an electrical length of about 10 centimeters.

10. The method of claim 2 wherein said MRI probe further comprises an insulator tube.

11. The method of claim 10 wherein said insulator tube has a diameter in the range of about 3 to 14 French.

12. The method of claim 10 wherein said insulator tube has a diameter in the range of about 9 French.

13. The method of claim 2, further comprising providing an access structure suitable for insertion into the esophagus and passing the MRI probe through the access structure into the esophagus.

14. A method for evaluating mediastinal anatomy, comprising:

providing a MRI probe adapted for insertion into a mediastinum;

providing an access structure suitable for insertion into the mediastinum and dimensionally adapted for passing the MRI probe into the mediastinum;

inserting the access structure into the mediastinum;

passing the MRI probe through the access structure into the mediastinum; and obtaining signals from the MRI probe that delineate the mediastinal anatomy.

15. A method for diagnosing an abnormality of a mediastinum, comprising:

providing a MRI probe adapted for insertion into the mediastinum;

inserting the MRI probe into the mediastinum;

obtaining from the MRI probe images of an anatomic area within the mediastinum; and evaluating the images to identify the abnormality.

16. The method of claim 15, further comprising:

providing an access structure dimensionally adapted for insertion into the mediastinum and further dimensionally adapted to receive the MRI probe therethrough; and inserting the MRI probe through the access structure, thereby positioning it within the mediastinum.

17. The method of claim 15, further comprising sampling the abnormality identified from the images obtained from the MRI probe.

18. The method of claim 17, wherein the sampling is performed using a biopsy tool.

19. The method of claim 18, wherein the biopsy tool is inserted into the mediastinum using a second access structure, said second access structure dimensionally adapted for the passage of the biopsy tool into the mediastinum.

20. A system for evaluating an anatomic area of a mediastinum, comprising:

a MRI probe dimensionally adapted for positioning within the mediastinum, wherein said probe produces MRI signals representing the anatomic area of the mediastinum;

an access structure dimensionally adapted for entering the mediastinum and further dimensionally adapted for passing the MRI probe therethrough to enter the mediastinum; and a signal processor that receives signals produced by the MRI probe and generates from the signals images related to the anatomic area; and a display for displaying the images.

21. A method for treating an abnormality of a mediastinum, comprising:

positioning a MRI probe within the mediastinum;

generating from the MRI probe signals that produce an image of the abnormality; and directing a therapeutic intervention towards the abnormality guided by the image of the abnormality produced from the MRI probe signals.

22. An MRI probe, comprising:

an antenna; and a probe shaft;

wherein said antenna and said probe shaft are adapted for insertion into an esophagus.

23. The MRI probe of claim 22 wherein said antenna is a loop design.

24. The MRI probe of claim 22 wherein said antenna is a loopless design.

25. A method for evaluating pancreaticohepaticobiliary anatomy, comprising:

providing a MRI probe dimensionally adapted for insertion into a pancreaticohepaticobiliary structure;

inserting the MRI probe into the pancreaticohepaticobiliary structure; and obtaining from the MRI probe signals related to pancreaticohepaticobiliary anatomy.

26. The method of claim 25, further comprising providing an access structure suitable for insertion into the pancreaticohepaticobiliary structure, and passing the MRI probe through the access structure into the pancreaticohepaticobiliary structure.

27. The method of claim 26, wherein the access structure is adapted for insertion through a common bile duct.

28. The method of claim 27, wherein the insertion through the common bile duct further comprises insertion through a duodenum to reach the common bile duct.

29. The method of claim 26, wherein the access structure is adapted for insertion through a gallbladder.

30. A system for evaluating pancreaticohepaticobiliary anatomy, comprising:

a MRI probe dimensionally adapted for positioning within a pancreaticohepaticobiliary structure, wherein said probe produces signals representing pancreaticohepaticobiliary anatomy;

a signal processor that receives signals produced by the MRI probe and generates from the signals images related to the anatomy; and a display for displaying the images.

31. The system of claim 30, further comprising an access structure dimensionally adapted for insertion into a pancreaticohepaticobiliary structure and further dimensionally adapted for receiving therethrough the MRI probe.

32. A method for diagnosing an abnormality of a pancreaticohepaticobiliary system, comprising:

providing a MRI probe dimensionally adapted for insertion into the pancreaticohepaticobiliary system;

inserting the MRI probe into the pancreaticohepaticobiliary system;

obtaining from the MRI probe images of an anatomic area within the pancreaticohepaticobiliary system; and evaluating the images to identify the abnormality.

33. The method of claim 32, further comprising:

providing an access structure dimensionally adapted for insertion into the pancreaticohepaticobiliary system and further dimensionally adapted to receive the MRI probe therethrough; and inserting the MRI probe through the access structure, thereby positioning it within the pancreaticohepaticobiliary system.

34. The method of claim 32 further comprising sampling the abnormality identified from the images obtained from the MRI probe.

35. The method of claim 34, wherein the sampling is performed using a biopsy tool.

36. The method of claim 35, wherein the biopsy tool is inserted into the pancreaticohepaticobiliary system using a second access structure, said second access structure dimensionally adapted for the passage of the biopsy tool into the pancreaticohepaticobiliary system.

37. A method for treating an abnormality of a pancreaticohepaticobiliary system, comprising:
 positioning a MRI probe within the pancreaticohepaticobiliary system;
 generating from the MRI probe signals that produce an image of the abnormality; and
 directing a therapeutic intervention towards the abnormality guided by the image of the abnormality produced from the MRI signals.

38. An MRI probe, comprising:
 an antenna; and
 a probe shaft;
 wherein said antenna and said probe shaft are adapted for insertion into a pancreaticohepaticobiliary structure.

39. The MRI probe of claim 38 wherein said antenna is a loop design.

40. The MRI probe of claim 38 wherein said antenna is a loopless design.

41. A method for evaluating tracheobronchopulmonary anatomy, comprising:
 providing a MRI probe dimensionally adapted for insertion into an anatomic structure selected from the group including the trachea, the bronchi, the bronchioles, the lung parenchyma and the intrapleural space;
 inserting the MRI probe into the anatomic structure; and
 obtaining from the MRI probe signals related to tracheobronchopulmonary anatomy.

42. The method of claim 41, further comprising providing an access structure suitable for insertion into the anatomic structure, and passing the MRI probe through the access structure into the anatomic structure.

43. A system for evaluating tracheobronchopulmonary anatomy, comprising:
 a MRI probe dimensionally adapted for positioning within an anatomic structure selected from the group consisting of the trachea, the bronchi, the bronchioles, the lung parenchyma and the intrapleural space, wherein said probe produces signals representing the anatomic structure;
 a signal processor that receives signals produced by the MRI probe and generates from the signals images related to the anatomic structure; and
 a display for displaying the images.

44. The system of claim 43, further comprising an access structure dimensionally adapted for insertion into the anatomic structure and further dimensionally adapted for receiving therethrough the MRI probe.

45. A method for diagnosing an abnormality of a tracheobronchopulmonary system, comprising:
 providing a MRI probe dimensionally adapted for insertion into an anatomic structure selected from the group consisting of the trachea, the bronchi, the bronchioles, the lung parenchyma and the intrapleural space;
 inserting the MRI probe into the anatomic structure;
 obtaining from the MRI probe images of an anatomic area within the tracheobronchopulmonary system; and
 evaluating eimagesto identify the abnormality.

46. The method of claim 45, further comprising:
 providing an access structure dimensionally adapted for insertion into the anatomic structure and further dimensionally adapted to receive the MRI probe therethrough; and
 inserting the MRI probe through the access structure, thereby positioning it within the tracheobronchopulmonary system.

47. The method of claim 45, further comprising sampling the abnormality identified from the images obtained from the MRI probe.

48. The method of claim 47, wherein the sampling is performed using a biopsy tool.

49. The method of claim 48, wherein the biopsy tool is inserted into the tracheobronchopulmonary system using a second access structure, said second access structure dimensionally adapted for the passage of the biopsy tool into the PHB system.

50. A method for treating an abnormality of a tracheobronchopulmonary system, comprising:
 positioning a MRI probe within the tracheobronchopulmonary system;
 generating from the MRI probe signals that produce an image of the abnormality; and
 directing a therapeutic intervention towards the abnormality guided by the image of the abnormality produced from the MRI signals.

51. An MRI probe, comprising:
 an antenna; and
 a probe shaft;
 wherein said antenna and said probe shaft are adapted for insertion into an anatomic structure selected from the group including the trachea, the bronchi, the bronchioles, the lung parenchyma, and the intrapleural space.

52. The MRI probe of claim 51 wherein said antenna is a loop design.

53. The MRI probe of claim 51 wherein said antenna is a loopless design.

54. A method for evaluating head and neck anatomy, comprising:
 providing a MRI probe dimensionally adapted for insertion into an anatomic structure selected from the group including the mouth, the nose, the pharynx, the larynx, the ear, the Eustachian tube, the salivary gland ducts, the sinuses, the orbit, the nasolacrimal duct, the globe, the carotid artery, and the distal vasculature;
 inserting the MRI probe into the anatomic structure; and
 obtaining from the MRI probe signals related to head and neck anatomy.

55. The method of claim 54, further comprising providing an access structure suitable for insertion into the anatomic structure, and passing the MRI probe through the access structure into the anatomic structure.

56. A system for evaluating head and neck anatomy, comprising:
 a MRI probe dimensionally adapted for positioning within an anatomic structure selected from the group consisting of the mouth, the nose, the pharynx, the larynx, the ear, the Eustachian tube, the salivary gland ducts, the sinuses, the orbit, the nasolacrimal duct and the globe, wherein said probe produces signals representing head and neck anatomy;
 a signal processor that receives signals produced by the MRI probe and generates from the signals images related to the anatomy; and
 display for displaying the images.

57. The system of claim 56, further comprising an access structure dimensionally adapted for insertion into the anatomic structure and further dimensionally adapted for receiving therethrough the MRI probe.

58. A method for diagnosing an abnormality of the head and neck, comprising:

providing a MRI probe dimensionally adapted for insertion into an anatomic structure selected from the group consisting of the mouth, the nose, the pharynx, the larynx, the ear, the Eustachian tube, the salivary gland ducts, the sinuses, the orbit, the nasolacrimal duct and the globe;

inserting the MRI probe into the anatomic structure;

obtaining from the MRI probe images of an anatomic area within the head and neck area; and evaluating the images to identify the abnormality.

59. The method of claim 58, further comprising:

providing an access structure dimensionally adapted for insertion into the anatomic structure, and further dimensionally adapted to receive the MRI probe therethrough; and inserting the MRI probe through the access structure, thereby positioning it within the anatomic structure.

60. The method of claim 58, further comprising sampling the abnormality identified from the images obtained from the MRI probe.

61. The method of claim 60, wherein the sampling is performed using a biopsy tool.

62. The method of claim 61, wherein the biopsy tool is inserted into a second anatomic structure selected from the group consisting of the mouth, the nose, the pharynx, the larynx, the ear, the Eustachian tube, the salivary gland ducts, the sinuses, the skin, the muscles, the orbit, the nasolacrimal duct and the globe in order to gain access to the abnormality of the head and neck.

63. A method for treating an abnormality of the head and neck, comprising:

positioning a MRI probe within an anatomic structure selected from the group consisting of the mouth, the nose, the pharynx, the larynx, the ear, the Eustachian tube, the salivary gland ducts, the sinuses, the orbit, the nasolacrimal duct and the globe;

generating from the probe MRI signals that produce an image of the abnormality; and directing a therapeutic intervention towards the abnormality guided by the image of the abnormality produced from the MRI signals.

64. An MRI probe, comprising:

an antenna; and a probe shaft;

wherein said antenna and said probe shaft are adapted for insertion into an anatomic structure selected from the group including the mouth, the nose, the pharynx, the larynx, the ear, the Eustachian tube, the salivary gland ducts, the sinuses, the orbit, the nasolacrimal, and the globe.

65. The MRI probe of claim 64 wherein said antenna is a loop design.

66. The MRI probe of claim 64 wherein said antenna is a loopless design.

67. A method for evaluating genitourinary anatomy, comprising:

providing a MRI probe dimensionally adapted for insertion into an anatomic structure selected from the group consisting of the urethra, the ureter, the bladder, the renal pelvis, the anus, the vagina, the cervix, the fallopian tube, the pouch of Douglas and space of Retzius;

inserting the MRI probe into the anatomic structure; and obtaining from the MRI probe signals related to genitourinary anatomy.

68. The method of claim 67, wherein said MRI probe has a diameter in the range of about 0.5 to 55 French.

69. The method of claim 67, wherein said MRI probe has a diameter in the range of about 0.5 to 9 French.

70. The method of claim 67, wherein said MRI probe has a diameter in the range of about 0.5 to 3 French.

71. The method of claim 67, wherein said MRI probe has a diameter of about 3 French.

72. The method of claim 67, wherein said MRI probe has a diameter of about 4 French.

73. The method of claim 67, wherein said MRI probe has a diameter of about 9 French.

74. The method of claim 67 wherein said MRI probe has a length in the range of about 5 to 150 centimeters.

75. The method of claim 67 wherein said MRI probe has a length in the range of about 20 to 70 centimeters.

76. The method of claim 67 wherein said MRI probe has a length in the range of about 30 to 35 centimeters.

77. The method of claim 67 wherein said probe is "C" shaped.

78. The method of claim 67 wherein said MRI probe comprises an antenna.

79. The method of claim 78 wherein said antenna has a length in the range of about 1 to 30 centimeters.

80. The method of claim 78 wherein said antenna has a length of about 2 to 20 centimeters.

81. The method of claim 78 wherein said antenna has a length of about 7 centimeters.

82. The method of claim 78 wherein said antenna has a length of about 10 centimeters.

83. The method of claim 78 wherein said antenna has a length of about 20 centimeters.

84. The method of claim 67 wherein said MRI probe further comprises an insulator tube.

85. The method of claim 84 wherein said insulator tube has a diameter in the range of about 2 to 60 French.

86. The method of claim 84 wherein said insulator tube has a diameter in the range of about 9 to 15 French.

87. The method of claim 67, further comprising providing an access structure suitable for insertion into the anatomic structure, and passing the MRI probe through the access structure into the anatomic structure.

88. A system for evaluating genitourinary anatomy, comprising:

a MRI probe dimensionally adapted for positioning within an anatomic structure selected from the group consisting of the urethra, the ureter, the bladder, the renal pelvis, the anus, the vagina, the cervix, the fallopian tube and the pouch of Douglas and space of Retzius, wherein said probe produces signals representing genitourinary anatomy;

a signal processor that receives signals produced by the MRI probe and generates from the signals images related to the anatomy; and a display for displayng the images.

89. The system of claim 88, further comprising an access structure dimensionally adapted for insertion into the anatomic structure and further dimensionally adapted for receiving therethrough the MRI probe.

90. A method for diagnosing a genitourinary abnormality, comprising:

providing a MRI probe dimensionally adapted for insertion into an anatomic structure selected from the group consisting of the urethra, the ureter, the bladder, the renal pelvis, the anus, the vagina, the cervix, the fallopian tube and the pouch of Douglas and space of Retzius;

inserting the MRI probe into the anatomic structure;
obtaining from the MRI probe images of an anatomic area within the genitourinary area; and
evaluating the images to identify the abnormality.

91. The method of claim 90, further comprising:
providing an access structure dimensionally adapted for insertion into the anatomic structure, and further dimensionally adapted to receive the MRI probe therethrough; and
inserting the MRI probe through the access structure, thereby positioning it within the anatomic structure.

92. The method of claim 90, further comprising sampling the abnormality identified from the images obtained from the MRI probe.

93. The method of claim 92, wherein the sampling is performed using a biopsy tool.

94. The method of claim 93, wherein the biopsy tool is inserted into a second anatomic structure selected from the group consisting of the of the urethra, the ureter, the bladder, the renal pelvis, the anus, the vagina, the cervix, the fallopian tube, the peritoneal cavity, the pouch of Douglas and space of Retzius in order to gain access to the abnormality.

95. A method for treating a genitourinary abnormality, comprising:
positioning a MRI probe within an anatomic structure selected from the group consisting of the urethra, the ureter, the bladder, the renal pelvis, the anus, the vagina, the cervix, the fallopian tube and the pouch of Douglas and space of Retzius;
generating from the probe MRI signals that produce an image of the abnormality; and
directing a therapeutic intervention towards the abnormality guided by the image of the abnormality produced from the MRI signals.

96. An MRI probe, comprising:
an antenna; and
a probe shaft;
wherein said antenna and said probe shaft are adapted for insertion into an anatomic structure selected from the group including the urethra, the ureter, the bladder, the renal pelvis, the anus, the vagina, the cervix, the fallopian tube, the Pouch of Douglas, and the space of Retzius.

97. The MRI probe of claim 96 wherein said antenna is a loop design.

98. The MRI probe of claim 96 is a loopless design.

99. A method for diagnosing an internal fluid collection, comprising:
providing a MRI probe dimensionally adapted for insertion into the internal fluid collection;
inserting the MRI probe into the internal fluid collection; and
obtaining from the MRI probe signals related to anatomic structures surrounding the internal fluid collection.

100. The method of claim 99, wherein the internal fluid collection comprises a cyst, a pseudocyst or a pus collection.

101. The method of claim 99, further comprising providing an access structure suitable for insertion into the internal fluid collection, and passing the MRI probe through the access structure into the internal fluid collection.

102. The method of claim 101, further comprising removing contents of the internal fluid collection through the access structure.

103. The method of claim 101, further comprising injecting an agent into the internal fluid collection through the access structure.

104. A method for evaluating gastrointestinal anatomy, comprising:
providing a MRI probe dimensionally adapted for insertion into an anatomic structure selected from the group consisting of the esophagus, the stomach, the duodenum, the jejunum, the ileum, the appendix, the colon and the rectum;
inserting the MRI probe into the anatomic structure; and
obtaining from the MRI probe signals related to gastrointestinal anatomy.

105. The method of claim 104 wherein said MRI probe has a length in the range of about 50 to 300 centimeters.

106. The method of claim 104 wherein said MRI probe has a length about equal to that of an endoscope.

107. The method of claim 104 wherein said MRI probe has a length in the range of about 100 to 150 centimeters.

108. The method of claim 104 wherein said MRI probe has a length of about 100 centimeters.

109. The method of claim 104 wherein said MRI probe has a length of about 150 centimeters.

110. The method of claim 104 wherein said MRI probe comprises an antenna.

111. The method of claim 110 wherein said antenna has a length in the range of about 1 to 30 centimeters.

112. The method of claim 110 wherein said antenna has a length of about 2 to 10 centimeters.

113. The method of claim 104 wherein said MRI probe further comprises an insulator tube.

114. The method of claim 113 wherein said insulator tube has a diameter in the range of about 1 to 2.5 French.

115. The method of claim 113, wherein said insulator tube has a diameter in the range of about 10 to 20 French.

116. The method of claim 113, wherein said insulator tube has a diameter in the range of about 15 to 17 French.

117. The method of claim 113, wherein said insulator tube has a diameter of about ⅓ Inch.

118. The method of claim 104, further comprising providing an access structure suitable for insertion into the anatomic structure, and passing the MRI probe through the access structure into the anatomic structure.

119. A system for evaluating gastrointestinal anatomy, comprising:
a MRI probe dimensionally adapted for positioning within an anatomic structure selected from the group consisting of the esophagus, the stomach, the duodenum, the jejunum, the ileum, the appendix, the colon and the rectum, wherein said probe produces signals representing gastrointestinal anatomy;
a signal processor that receives signals produced by the MRI probe and generates from the signals images related to gastrointestinal anatomy; and
a display for displaying the images.

120. A method for diagnosing an abnormality of gastrointestinal anatomy, comprising:
providing a MRI probe dimensionally adapted for insertion into a gastrointestinal system;
inserting the MRI probe into the gastrointestinal system;
obtaining from the MRI probe images of the gastrointestinal anatomy; and
evaluating the images to identify the abnormality.

121. The method of claim 120, further comprising:
providing an access structure dimensionally adapted for insertion into the gastrointestinal system and further dimensionally adapted to receive the MRI probe therethrough; and inserting the MRI probe through the access structure, thereby positioning it within the gastrointestinal system.

122. The method of claim 120, further comprising sampling the abnormality identified from the images obtained from the MRI probe.

123. The method of claim 122, wherein the sampling is performed using a biopsy tool.

124. The method of claim 123, wherein the biopsy tool is inserted into the gastrointestinal system using a second access structure, said second access structure dimensionally adapted for the passage of the biopsy tool into the gastrointestinal system.

125. A method for treating an abnormality of gastrointestinal anatomy, comprising:
positioning a MRI probe within a gastrointestinal system;
generating from the MRI probe signals that produce an image of the abnormality; and
directing a therapeutic intervention towards the abnormality guided by the image of the abnormality produced from the MRI signals.

126. An MRI probe, comprising:
an antenna; and
a probe shaft;
wherein said antenna and said probe shaft are adapted for insertion into a gastrointestinal system.

127. The MRI probe of claim 126 wherein said antenna is a loop design.

128. The MRI probe of claim 126 wherein said antenna is a loopless design.

129. A method for evaluating anatomy of a vascular system, comprising:
providing a MRI probe adapted for insertion into the vascular system;
inserting the MRI probe into the vascular system; and
obtaining from the MRI probe signals related to anatomy of the vascular system.

130. The method of claim 129, further comprising providing an access structure suitable for intravascular insertion and passing the MRI probe through the access structure into the vascular system.

131. A method for evaluating anatomy of a vascular system, comprising:
providing a MRI probe adapted for insertion into the vascular system;
providing an access structure suitable for insertion into the vascular system and dimensionally adapted for passing the MRI probe into the vascular system;
inserting the access structure into the vascular system;
passing the MRI probe through the access structure into the vascular system; and
obtaining signals from the MRI probe that delineate the anatomy of the vascular system.

132. A method for diagnosing an abnormality of the vascular system, comprising:
providing a MRI probe adapted for intravascular insertion;
inserting the MRI probe into the vascular system;
obtaining from the MRI probe images of an area of the vascular system; and
diagnosing the abnormality by interpreting the images.

133. The method of claim 132, further comprising:
providing an access structure dimensionally adapted for intravascular insertion and further dimensionally adapted to receive the MRI probe therethrough; and
inserting the MRI probe through the access structure, thereby positioning it within the vascular system.

134. The method of claim 132, further comprising sampling the abnormality identified from the images obtained from the MRI probe.

135. The method of claim 134, wherein the sampling is performed using a biopsy tool.

136. The method of claim 135, wherein the biopsy tool is inserted into the vascular system using a second access structure, said second access structure dimensionally adapted for the passage of the biopsy tool into the vascular system.

137. A system for evaluating an anatomic area of the vascular system, comprising:
a MRI probe dimensionally adapted for positioning within the vascular system, wherein said probe produces MRI signals representing an anatomic area of the vascular system;
an access structure dimensionally adapted for entering the vascular system and further dimensionally adapted for passing the MRI probe therethrough to enter the vascular system;
a signal processor that receives signals produced by the MRI probe and generates from the signals images related to the anatomic area; and
a display for displaying the images.

138. A method for treating an abnormality of the vascular system, comprising:
positioning a MRI probe within the vascular system;
generating from the MRI probe signals that produce an image of the abnormality; and
directing a therapeutic intervention towards the abnormality guided by the image of the abnormality produced from the MRI probe signals.

139. An MRI probe, comprising:
an antenna; and
a probe shaft;
wherein said antenna and said probe shaft are adapted for intravascular insertion.

140. The MRI probe of claim 139 wherein said antenna is a loop design.

141. The MRI probe of claim 139 wherein said antenna is a loopless design.

142. A system for evaluating a perivascular structure, comprising:
a MRI probe dimensionally adapted for positioning within a vascular system, wherein said probe produces MRI signals representing the perivascular structure;
an access structure dimensionally adapted for entering the vascular system and further dimensionally adapted for passing the MRI probe therethrough to enter the vascular system;
a signal processor that receives signals produced by the MRI probe and generates from the signals images related to the perivascular structure; and
a display for displaying the images.

143. A method for diagnosing an abnormality of a perivascular structure, comprising:
providing a MRI probe adapted for intravascular insertion; positioning a MRI probe within a vascular system;
directing the MRI probe through the vascular system towards the perivascular structure;
obtaining from the MRI probe images of the perivascular structure; and
evaluating the images to identify the abnormality.

144. The method of claim 143, further comprising sampling the abnormality identified from the images obtained from the MRI probe.

145. The method of claim 144, wherein the sampling is performed using a biopsy tool.

146. A method for treating an abnormality of a perivascular structure, comprising:

positioning a MRI probe within a vascular system;

directing the MRI probe through the vascular system towards the perivascular structure;

generating from the MRI probe signals that produce an image of the abnormality; and directing a therapeutic intervention towards the abnormality guided by the image of the abnormality produced from the MRI probe signals.

147. The method of claim 146, wherein access to the abnormality for performing the therapeutic intervention is provided by an extravascular route.

148. The method of claim 146, wherein access to the abnormality for performing the therapeutic intervention is provided by an intravascular route.

* * * * *